US010716894B2

United States Patent
Lee

(10) Patent No.: US 10,716,894 B2
(45) Date of Patent: Jul. 21, 2020

(54) MULTI-TYPE MEDICINAL FLUID FLOW RATE CONTROL APPARATUS AND MEDICINAL FLUID INJECTOR COMPRISING SAME

(71) Applicant: Woo Suk Lee, Seoul (KR)

(72) Inventor: Woo Suk Lee, Seoul (KR)

( * ) Notice: Subject to any disclaimer, the term of this patent is extended or adjusted under 35 U.S.C. 154(b) by 580 days.

(21) Appl. No.: 15/474,100

(22) Filed: Mar. 30, 2017

(65) Prior Publication Data

US 2017/0203034 A1    Jul. 20, 2017

Related U.S. Application Data

(63) Continuation of application No. PCT/KR2015/010279, filed on Sep. 30, 2015.

(30) Foreign Application Priority Data

Sep. 30, 2014   (KR) .......................... 10-2014-0131763

(51) Int. Cl.
   *A61M 5/168*    (2006.01)
   *A61M 5/142*    (2006.01)
   (Continued)

(52) U.S. Cl.
   CPC ........ *A61M 5/16813* (2013.01); *A61M 5/142* (2013.01); *A61M 5/16881* (2013.01);
   (Continued)

(58) Field of Classification Search
   CPC .......... A61M 5/16827; A61M 5/16813; A61M 5/16804; A61M 5/142; A61M 5/16877;
   (Continued)

(56) References Cited

U.S. PATENT DOCUMENTS

| 7,011,651 B2 | 3/2006 | Lee et al. |
| 8,512,284 B2 | 8/2013 | Lee |
| 2012/0053556 A1* | 3/2012 | Lee .................... A61M 5/16877 |
| | | 604/500 |

FOREIGN PATENT DOCUMENTS

| JP | H10-295811 A | 10/1998 |
| JP | 2006-500123 A | 1/2006 |

(Continued)

OTHER PUBLICATIONS

Korean Office Action (KR 10-2014-0131763), KIPO, dated Nov. 17, 2015.

(Continued)

*Primary Examiner* — Laura A Bouchelle
*Assistant Examiner* — Justin L Zamory
(74) *Attorney, Agent, or Firm* — Park & Associates IP Law, P.C.

(57) ABSTRACT

The present invention relates to a medicinal fluid flow rate control apparatus and a medicinal fluid injector including the medicinal fluid flow control apparatus. The medicinal fluid flow rate control apparatus includes: an operation knob being able to be turned; a plurality of medicinal fluid delivery lines each having an elastically deformable tube and arranged such that the tubes are arranged at different heights at a side from the operation knob; a tube support member supporting the tubes; a medicinal fluid converger converging medicinal fluids from the medicinal fluid delivery lines into one stream; and a pipe switch selectively pressing or releasing the tubes to open or block all of the medicinal fluid delivery lines or block some of the medicinal fluid delivery lines, depending on a rotational angle of the operation knob.

12 Claims, 25 Drawing Sheets

(51) Int. Cl.
*A61M 39/28* (2006.01)
*A61M 39/22* (2006.01)

(52) U.S. Cl.
CPC .......... *A61M 39/223* (2013.01); *A61M 39/28* (2013.01); *A61M 39/285* (2013.01)

(58) Field of Classification Search
CPC .. A61M 39/284; F16K 11/0853; F16K 11/163
See application file for complete search history.

(56) References Cited

FOREIGN PATENT DOCUMENTS

| | | |
|---|---|---|
| KR | 10-0472044 B1 | 3/2005 |
| KR | 10-0880358 B1 | 1/2009 |
| KR | 10-1126213 B1 | 3/2012 |
| KR | 10-2014-0049836 A | 4/2014 |
| WO | 2004-026373 A1 | 4/2004 |
| WO | 2012-025814 A2 | 3/2012 |
| WO | 2014-062013 A1 | 4/2014 |

OTHER PUBLICATIONS

International Search Report (PCT/KR2015/010279), WIPO, dated Jan. 11, 2016.
Supplementary European Search Report (EP15 84 6382), EPO, dated Feb. 22, 2018.
Japan Office Action (JP2017-518267), JPO, dated Feb. 6, 2018.

* cited by examiner

MULTI-TYPE MEDICINAL FLUID FLOW RATE CONTROL APPARATUS AND MEDICINAL FLUID INJECTOR COMPRISING SAME

REFERENCE TO RELATED APPLICATIONS

This is a continuation of International Patent Application PCT/KR2015/010279 filed on Sep. 30, 2015, which designates the United States and claims priority of Korean Patent Application No. 10-2014-0131763 filed on Sep. 30, 2014, the entire contents of which are incorporated herein by reference.

FIELD OF THE INVENTION

The present invention relates to a control apparatus that controls the dosage (flow rate) of medicinal fluid when injecting medicinal fluid such as an anodyne or an antibiotic into a patient, and a medicinal fluid injector including the control apparatus.

BACKGROUND OF THE INVENTION

In general, cancer patients are treated by injection of special antibiotics, and patients who need pain management are treated by injection of anodynes for reducing pain. When medicinal fluids such as special antibiotics or anodynes are excessively provided, unlike other general medicinal fluids, they may cause patients to lapse into a comatose state or suffer death from shock. However, when such fluids are not sufficiently provided, the purposes of the medicinal fluids cannot be obtained. Accordingly, it is very important to inject an accurate amount within an allowable range.

Syringes have been used to inject medicinal fluids in most cases of the related art. However, when syringes were used, the dosage of medicinal fluids depended on the skill level of people who handle the syringes, etc. and they were necessarily involved every time the patient required an injection of medicinal fluids, so it was very difficult to maintain dosage per hour at an appropriate level. That is, it is difficult to manage and maintain the dosage of medicinal fluids.

Further, dosage adjusters that are installed on hoses for injecting medicinal fluid have been used to adjust the dosage of the medicinal fluids. However, the dosage was adjusted by the degree of pressing the hoses by the dosage adjusters, so it was difficult to accurately inject a desired amount of medicinal fluids in accordance with the momentarily changing states of patients.

SUMMARY OF THE INVENTION

Technical Problem

An object of an embodiment of the present invention is to provide a medicinal fluid flow rate control apparatus that can more accurately adjust the dosage of medicinal fluids so that a necessary amount of medicinal fluids can be injected, and a medicinal fluid injector including the apparatus.

Technical Solution

According to an embodiment of the present invention, a medicinal fluid flow rate control apparatus includes: an operation knob being able to be turned; a plurality of medicinal fluid delivery lines each having an elastically deformable tube and arranged such that the tubes are arranged at different heights at a side from the operation knob; a tube support member supporting the tubes such that the tubes are positioned between the operation knob and the tube support member; a medicinal fluid converger converging medicinal fluids from the medicinal fluid delivery lines into one stream; and a pipe switch selectively pressing or releasing the tubes to open all of the medicinal fluid delivery lines or block at least any one of the medicinal fluid delivery lines, depending on a rotational angle of the operation knob.

The pipe switch may include: a plurality of spring plates disposed at heights corresponding to the tubes, respectively, between the operation knob and the tubes, and pressing the tubes at the heights by bending toward the tubes when coming in contact with an outer side of the operation knob; and recessions formed at least at one position on the outer side of the operation knob at the heights corresponding to the spring plates, respectively, formed in a concave shape, and allowing the corresponding spring plates to restore so that the tubes pressed by the corresponding spring plates are released when being aligned with the corresponding spring plates, and the recessions at the heights may be arranged such that the tubes pressed by the spring plates are all released or at least any one of the tubes are pressed by the spring plates, depending on the rotational angle of the operation knob.

The spring plates may each have a pressing portion formed on a side facing the tubes and a projection formed on a side facing the operation knob to come in contact with the outer side of the operation knob or move into the recessions.

Seats where the tubes are seated, respectively, may be formed at the tube support member, the tubes in the seats may be prevented from separating by a cover coupled to both sides of the tube support member and covering both ends of the seats, and both ends of the spring plates may be connected to the covers at both sides, respectively.

According to an embodiment of the present invention, a medicinal fluid injector includes: an operation knob being able to be turned; a first delivery line diverging from a medicinal fluid inflow line and connected to a medicinal fluid discharge line; a medicinal fluid pumping unit disposed in the first delivery line, keeping a medicinal fluid flowing through the first delivery line, and pumping the kept medicinal fluid to the medicinal fluid discharge line; a plurality of second delivery lines diverging from the medicinal fluid inflow line, each having an elastically deformable tube, and arranged such that the tubes are arranged at different heights at a side from the operation knob; a tube support member supporting the tubes such that the tubes are positioned between the operation knob and the tube support member; a medicinal fluid converger connected to the medicinal discharge line and converging medicinal fluids from the second delivery lines into one stream; and a pipe switch selectively pressing or releasing the tubes to open all of the second delivery lines or block at least any one of the second delivery lines, depending on a rotational angle of the operation knob.

The injector may further include: a case in which the operation knob and the medicinal fluid pumping unit are installed to be operated from the outside; and a rotational angle determiner disposed between the operation knob and the case to determine a position such that the operation knob can be turned at a predetermined angle.

The rotational angle determiner may have: a plurality of locking grooves formed at predetermined angles around a bottom of the operation knob; and a locking protrusion formed inside the case to be fitted into at least any one of the locking grooves, depending on a rotational angle of the operation knob.

According to an embodiment of the present invention, a medicinal fluid injector includes: an operation knob being able to be turned; a plurality of first delivery lines diverging from a medicinal fluid inflow line, each having an elastically deformable tube, and arranged such that the tubes are arranged at different heights at a side from the operation knob; a tube support member supporting the tubes such that the tubes are positioned between the operation knob and the tube support member; a medicinal fluid converger converging medicinal fluids from the first delivery lines into one stream; a converging line supplying the medicinal fluid from the medicinal fluid converger to a medicinal fluid discharge line; a medicinal fluid pumping unit disposed in the converging line, keeping the medicinal fluid from the first delivery lines, and pumping the kept medicinal fluid to the medicinal fluid discharge line; a second delivery line diverging from the medicinal fluid inflow line and connected to the medicinal fluid delivery line; and a pipe switch selectively pressing or releasing the tubes to open all of the first delivery lines or block at least any one of the first delivery lines, depending on a rotational angle of the operation knob.

Advantageous Effects

According to the present invention, it is possible to inject an accurate amount of medicinal fluid into a subject by accurately and finely adjusting the flow rate of the medicinal fluid.

DETAILED DESCRIPTION OF THE INVENTION

Preferred embodiments of the present invention are described hereafter with reference to the accompanying drawings.

[Medicinal Fluid Flow Fate Control Apparatus According to First Embodiment]

A medicinal fluid flow rate control apparatus according to the first embodiment of the present invention is shown in FIGS. 1 to 11.

Figure 1:
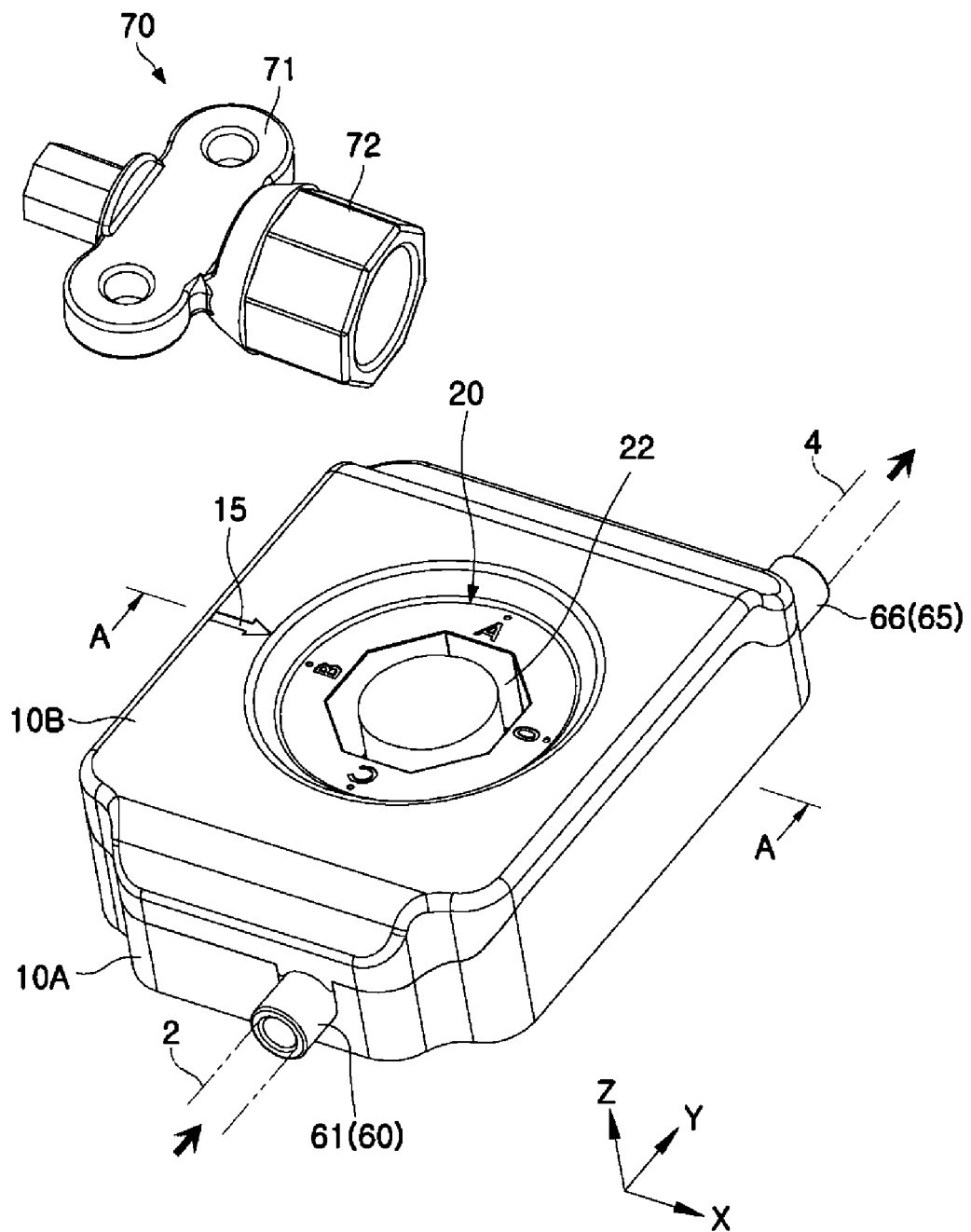
FIGS. 1 and 2 are a perspective view and an exploded perspective view showing a medicinal fluid flow rate control apparatus according to a first embodiment of the present invention.
Figure 2:
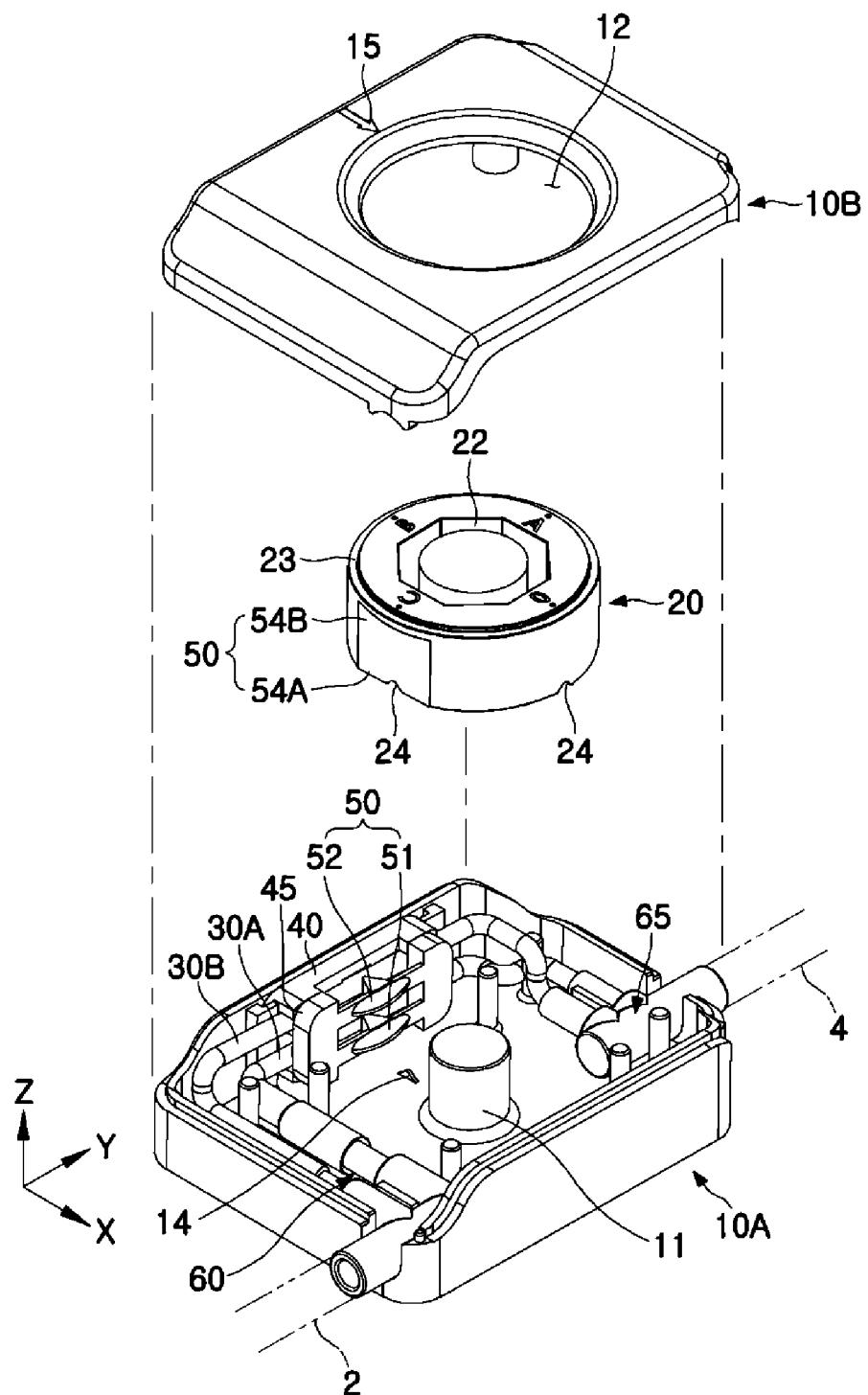

Referring to FIGS. 1 and 2, a medicinal fluid flow rate control apparatus according to the first embodiment of the present invention includes a first case 10A that is the lower part, a second case 10B that is the upper part combined with the first case 10A, an operation knob 20 that is operated by a user, and two medicinal fluid delivery lines 30A and 30B for delivering a medicinal fluid.

Figure 5:
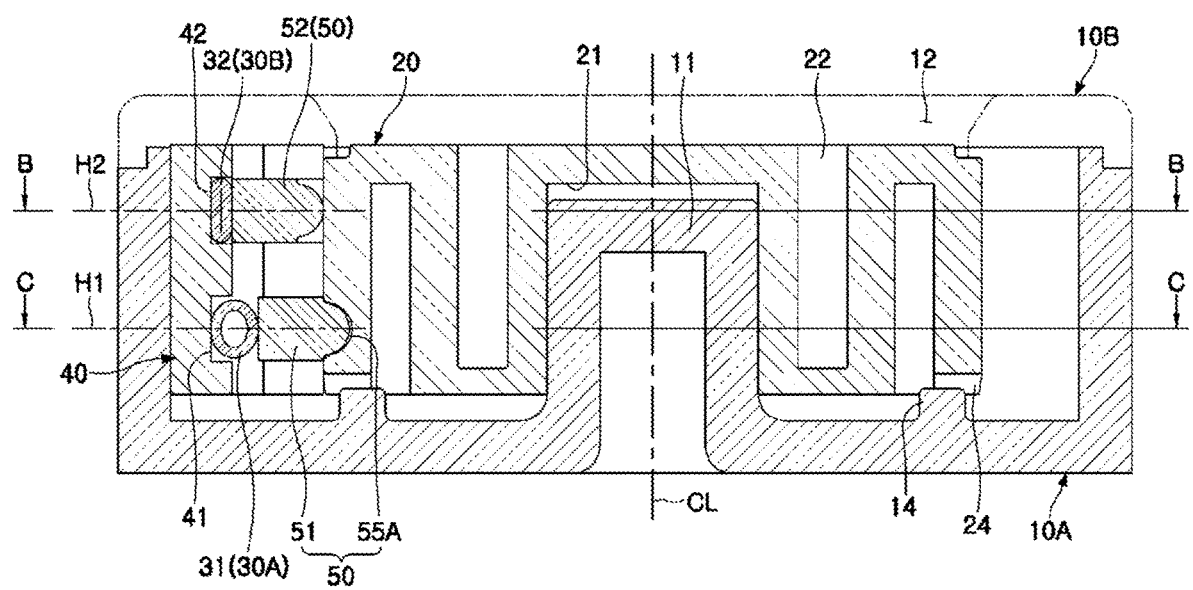
FIG. 5 is a cross-sectional view taken along line A-A shown in FIG. 1.

Referring to FIGS. 2 and 5, the operation knob 20 is disposed rotatably about a vertical axial line CL formed in the Z-axial direction in the cases 10a and 10B. In detail, a shaft 11 is vertically disposed on the bottom inside the first case 10A that is a case body, a center groove 21 in which the shaft 11 is inserted is vertically formed on the bottom of the operation knob 20, and the operation knob 20 is rotated on the shaft 11. A knob hole 12 for exposing the top of the operation knob 20 to the outside from the cases 10A and 10B is formed at the second case 10B that is a cover.

Figure 6:
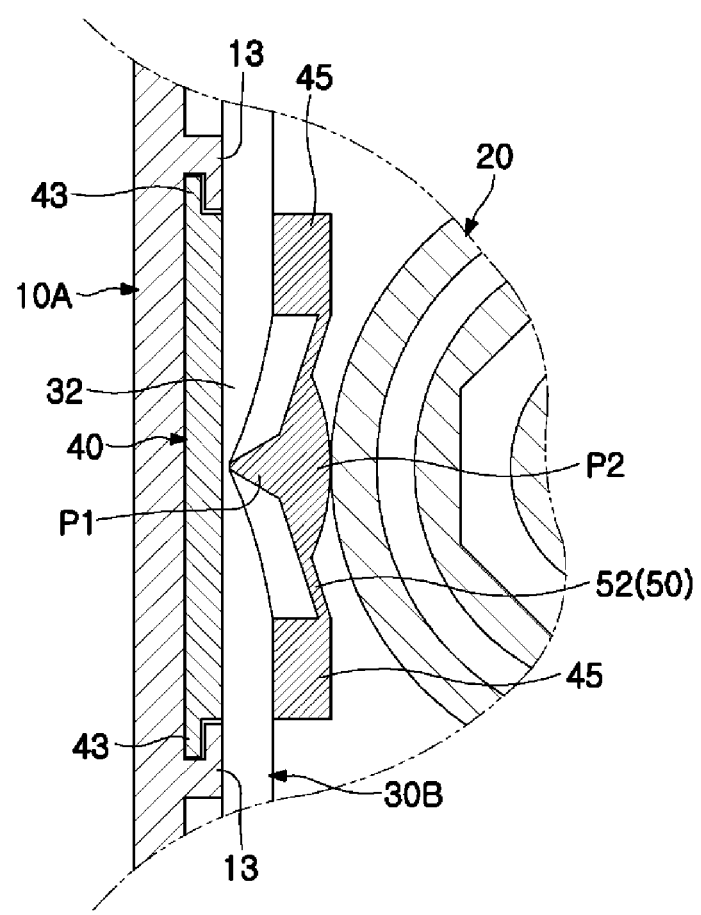
FIGS. 6 and 7 are cross-sectional views taken along lines B-B and C-C shown in FIG. 5.
Figure 7:
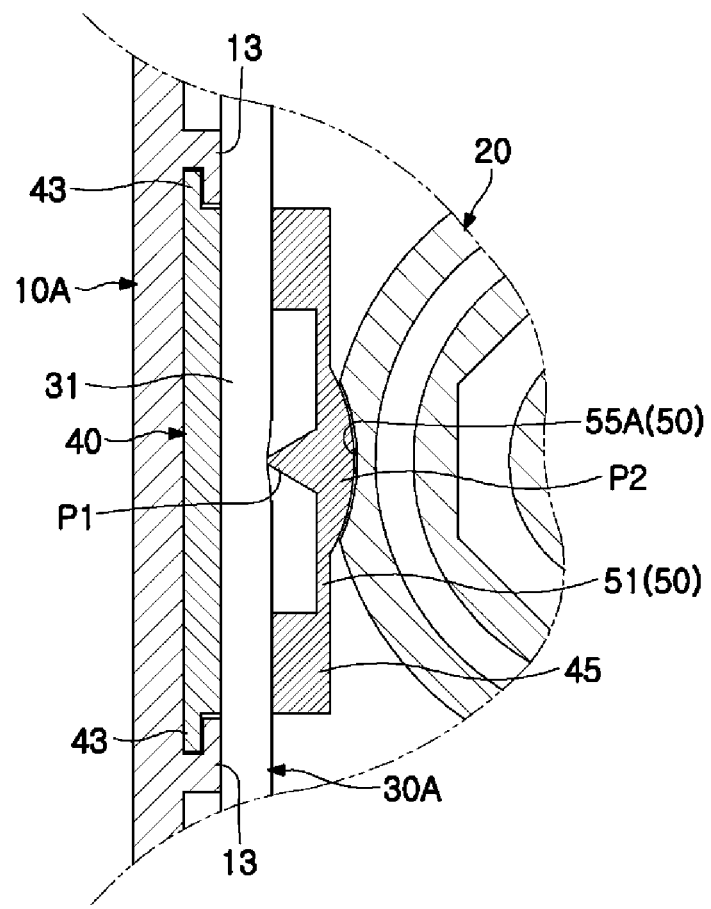

Referring to FIGS. 2, and 5 to 7, the medicinal fluid delivery lines 30A and 30B are made of elastic tubes 31 and 32, respectively. As shown in FIGS. 5 to 7, the medicinal fluid delivery lines 30A and 30B are composed of the tubes 31 and 32 positioned at different heights H1 and H2 at a side of the operation knob 20 in the cases 10A and 10B and the tubes 31 and 32 are concentrated at a side of the operation knob 20. The medicinal fluid delivery lines 30A and 30B may be partially or entirely made of the tubes 31 and 32. The tubes 31 and 32 may be arranged in the Y-axial direction. A silicon tube or a PVC tube that can be elastically deformed may be used for the tubes 31 and 32.

Figure 3:
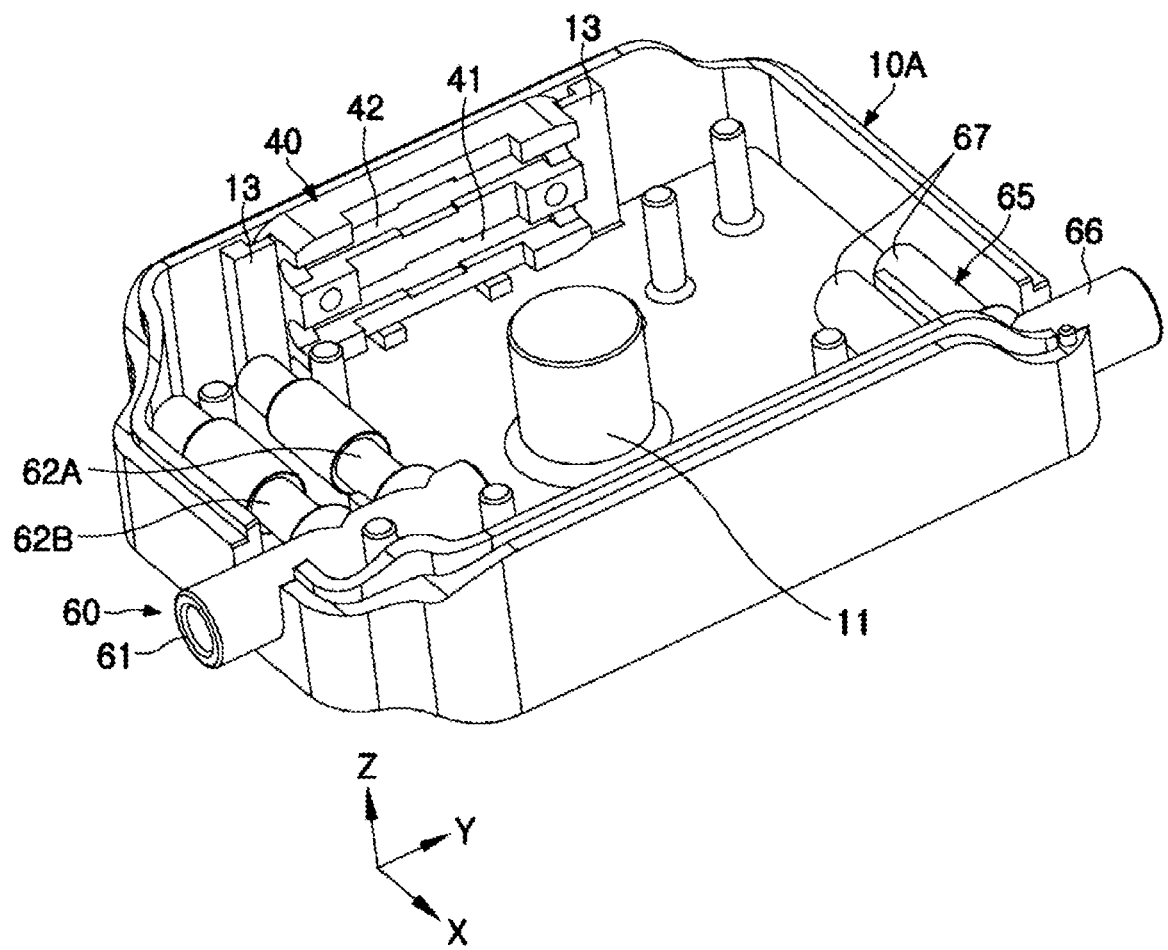
FIG. 3 is a perspective view showing the internal structure of the medicinal fluid flow rate control apparatus according to a first embodiment of the present invention.

Referring to FIGS. 3 and 5, a tube support member 40 that supports the tubes 31 and 32 is disposed in the cases 10A and 10B such that the tubes 31 and 32 are positioned between the tube support member 40 and the operation knob 20. Tube seats 41 and 42 where the tubes 31 and 32 are seated, respectively, at different heights H1 and H2 are formed in the longitudinal direction of the tube support member 40 on the front side facing the operation knob 20 of the tube support member 40.

As shown in FIGS. 3, 6, and 7, the tube support member 40 is detachably mounted on an inner side of the first case 10A. To this end, coupling steps 13 that form grooves between an inner side of the first case 10A and the coupling steps 13 are disposed at both sides on the inner side of the first case 10A and extensions 43 that are fitted in the grooves formed by the coupling steps 13 are formed at both longitudinal ends of the tub support member 40. The coupling steps 13 and the grooves 43 may be formed such that the tube support member 40 can be coupled by sliding down.

Referring to FIGS. 2, 6, and 7, the tubes 31 and 32 inserted in the tube seats 41 and 42 are held at the positions by seat covers 45 that are coupled to both longitudinal sides on the front side of the tube support member 40 to cover both ends of the tube seats 41 and 42.

Referring to FIGS. 2 to 5, the tubes 31 and 32 are pressed or released by a tube switch 50 so that the medicinal fluid delivery lines 30A and 30B are opened or closed in the cases 10A and 10B. A medicinal fluid distributor 60 that distributes a medicinal fluid at different flow rates into the medicinal fluid lines 30A and 30B and a medicinal fluid converger 65 that converges the medicinal fluids discharged from the medicinal fluid delivery lines 30A and 30B are disposed in the cases 10A and 10B. Reference numeral '70' in FIG. 1 indicates an operation handle for turning the operation knob 20.

As shown in FIG. 3, the medicinal fluid distributor 60 is composed of a inflow pipe 61 through which a medicinal fluid flows inside through a medicinal fluid supplier and two flow rate control pipes 62A and 62B diverging from the inflow pipe 61 and connected to first ends of the medicinal fluid delivery lines 30A and 30B, respectively. The inflow pipe 61 has an inlet outside the cases 10A and 10B and the flow rate control pipes 62A and 62B are disposed inside the cases 10A and 10B. As in FIGS. 1 and 2, a medicinal fluid inflow hose 2 that is a medicinal fluid inflow line for delivering a medicinal fluid from the medicinal fluid supplier is connected to the inlet of the inflow pipe 61. Capillary tubes having different cross-sectional areas may be used for the flow rate control pipes 62A and 62B.

The medicinal fluid converger 65 is composed of a converging pipe 66 and two diverging pipes 67 diverging from the converging pipe 66 and connected to second ends of the medicinal fluid delivery lines 30A and 30B. The converging pipe 66 has an outlet outside the cases 10A and 10B and the diverging pipes 67 are disposed inside the cases 10A and 10B. As shown in FIGS. 1 and 2, a medicinal fluid discharge hose 4 that is a medicinal fluid discharge line for delivering the medicinal fluid from the converging pipe 66 to a desired place (a patient etc.) is connected to the outlet of the converging pipe 66. An injection unit (such as the needle of a syringe or a catheter) for injecting a medicinal fluid into a subject (a patient etc.) may be connected to the medicinal fluid discharge hose 4.

Diverging pipes instead of the flow rate control pipes 62A and 62 may be provided for the medicinal fluid distributor 60 and flow rate control pipes instead of the diverging pipes 67 may be provided for the medicinal fluid converger 65. Alternatively, diverging pipes instead of the flow rate control pipes 62A and 62B may be provided for the medicinal fluid distributor 60 and the medicinal fluid delivery lines 30A and 30B may be partially composed of flow rate control pipes.

As shown in FIG. 1, the operation handle 70 is detachably coupled to the upper portion of the operation knob 20 through the knob hole 12 from the outside of the cases 10A and 10B. To this end, a coupling groove 22 is vertically formed on the top of the operation knob 20 and the operation handle 70 has a coupling rod 72 extending from a grip 71 of the operation handle 70 to be fitted into the coupling groove 22.

When a user puts the coupling rod 72 into the coupling groove 22 and then turns the operation handle 70 using the grip 71, the operation knob 20 is turned in the same as the operation handle 70. In order that the operation knob 20 is operated only by the operation handle 70, the coupling groove 22 may have a rounded inner side and a polygonal (e.g. octagonal) outer side and the coupling rod 72 may be formed in a shape corresponding to the shape of the coupling groove 22.

Referring to FIGS. 2, and 4 to 7, the tube switch 50 controls the flow rate of the medicinal fluid discharged from the converging pipe 66 by opening or closing both of the medicinal fluid delivery lines 30A and 30B or selectively closing the medicinal fluid delivery lines 30A and 30B, depending on the rotational angle of the operation knob 20.

The tube switch 50 includes two spring plates 51 and 52 disposed between the operation knob 20 and the tubes 31 and 32 and a plurality of recessions 54A, 55A, 54B, and 55B.

As shown in FIGS. 5 to 7, the spring plates 51 and 52 are positioned at the same heights H1 and H2 of the tubes 31 and 32 in contact with the outer rounded surface of the operation knob 20, so they selectively block the medicinal fluid delivery lines 30A and 30B by elastically bending toward and pressing the tubes 31 and 32 at the positions H1 and H2.

The recessions 54A, 55A, 54B, and 55B are formed in a concave shape at least at one position at the heights H1 and H2 corresponding to the spring plates 51 and 52. When the operation knob 20 is turned and the recessions 54A, 55A, 54B, and 55B reach the spring plates 51 and 52 at the heights H1 and H2, the spring plates 51 and 52 bending at the heights H1 and H2 are inserted back into the recessions, so the tubes 31 and 32 pressed by the spring plates 51 and 52 are released. That is, the medicinal fluid delivery lines 30A and 30B are selectively opened.

The spring plates 51 and 52 may be made of elastic metal or synthetic resin. As shown in FIGS. 2, 6, and 7, the longitudinal both ends of the spring plates 51 and 52 are connected to the seat covers 45 at both sides. The spring plates 51 and 52 may be integrated with the seat covers 45.

As shown in FIGS. 6 and 7, the spring plates 51 and 52 each have a pressing portion P1 protruding toward the tubes 31 and 42 from the sides facing the tubes 31 and 32. When the spring plates 51 and 52 are bent convexly toward the tubes 31 and 32, the pressing portion P1 press and block (close) the tubes 31 and 32. The pressing portion P1 may be pointed. The spring plates 51 and 52 each have a projection P2 that is formed on the sides facing the operation knob 20 to come in contact with the outer side of the operation knob 20 or to be inserted into the recessions 54A, 55A, 54B, and 55B.

Figure 4:
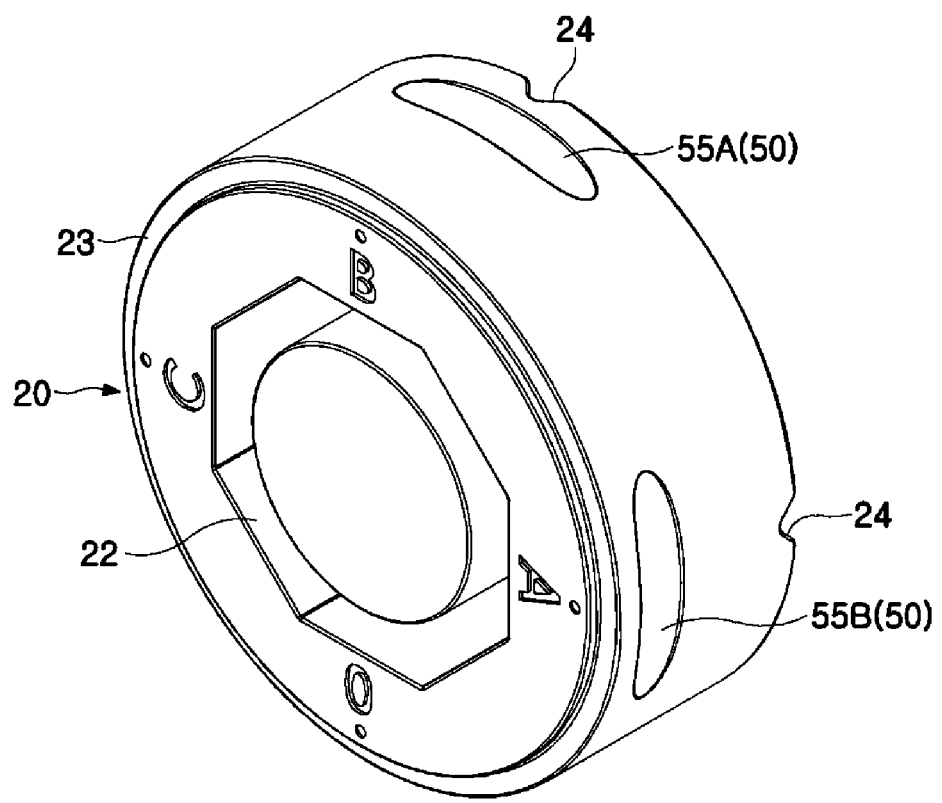
FIG. 4 is a perspective view showing the operation knob shown in FIGS. 1 and 2.

Referring to FIGS. 2, 4, and 5, the recessions 54A, 55A, 54B, and 55B are respectively formed at two positions at each of the heights H1 and H2 corresponding to the spring plates 51 and 52. In detail, as shown in FIGS. 2 and 4, the first recession 54A and the second recession 55A at the first height H1 are arranged at 90 degrees on and around the operation knob 20. Further, the first recession 54B at the second height H2 higher than the first height H1 is positioned in the same vertical line as the first recession 54A at the first height H1 and the second recession 55B at the second height H2 at the second height H2 and the first recession 54B at the second height are arranged at 180 degrees on and around the operation knob 20. The first recession 54A at the first height H1 and the first recession 54B at the second height H2 may integrally communicate with each other.

According to the arrangement of the recessions 54A, 55A, 54B, and 55B, when the operation knob 20 is turned by 90 degrees at each time, the tubes 31 and 32 of the medicinal fluid delivery lines 30A and 30B are both or selectively opened or blocked by being pressed or released by the spring plates 51 and 52.

In FIGS. 2 and 4, reference numeral '23' indicates a locking step. The locking step 23 is locked to the inner edge of the knob hole 12, thereby preventing the operation knob 20 from being pulled upward.

Reference numerals '14' and '24' in FIGS. 2, 4, and 5 indicate a rotational angle determiner for determining the rotational position of the operation knob 20 so that the operation knob 20 can be turned by 90 degrees at each time. The rotational angle determiner 14 and 24 is composed of four locking grooves 24 formed at 90 degrees along the bottom edge of the operation knob 20 around the center groove 21 and a locking projection 14 formed on the bottom of the first case 10A to be fitted into at least any one of the locking grooves 24, depending on the rotational angle of the operation knob 20. The locking projection 14 and at least one of the locking grooves 24 may have an inclined surface or a rounded surface for guiding so that the locking projection 14 can be smoothly fitted into and pulled out of the locking grooves 24. The positions of the locking projection 14 and the locking grooves 14 may be exchanged. Alternatively, only one locking groove 24 and four locking projections 14 may be formed.

When the medicinal fluid flow rate control apparatus according to the first embodiment of the present invention is configured such that, of the two flow rate control pipes 62A and 62B, a medicinal fluid flows at 2 mL/h through the flow rate control pipe 61A connected to the medicinal fluid delivery line 30A having the tube 31 at the first height H1 and a medicinal fluid flows at 1 mL/h through the flow rate control pipe 62B connected to the medicinal fluid delivery line 30B having the tube 32 at the second height H2, it is possible to adjust the amount of a medicinal fluid that is injected into a subject selectively in one of a total of four modes, as follows. These modes are described with reference to FIGS. 8 to 11.

Figure 8:
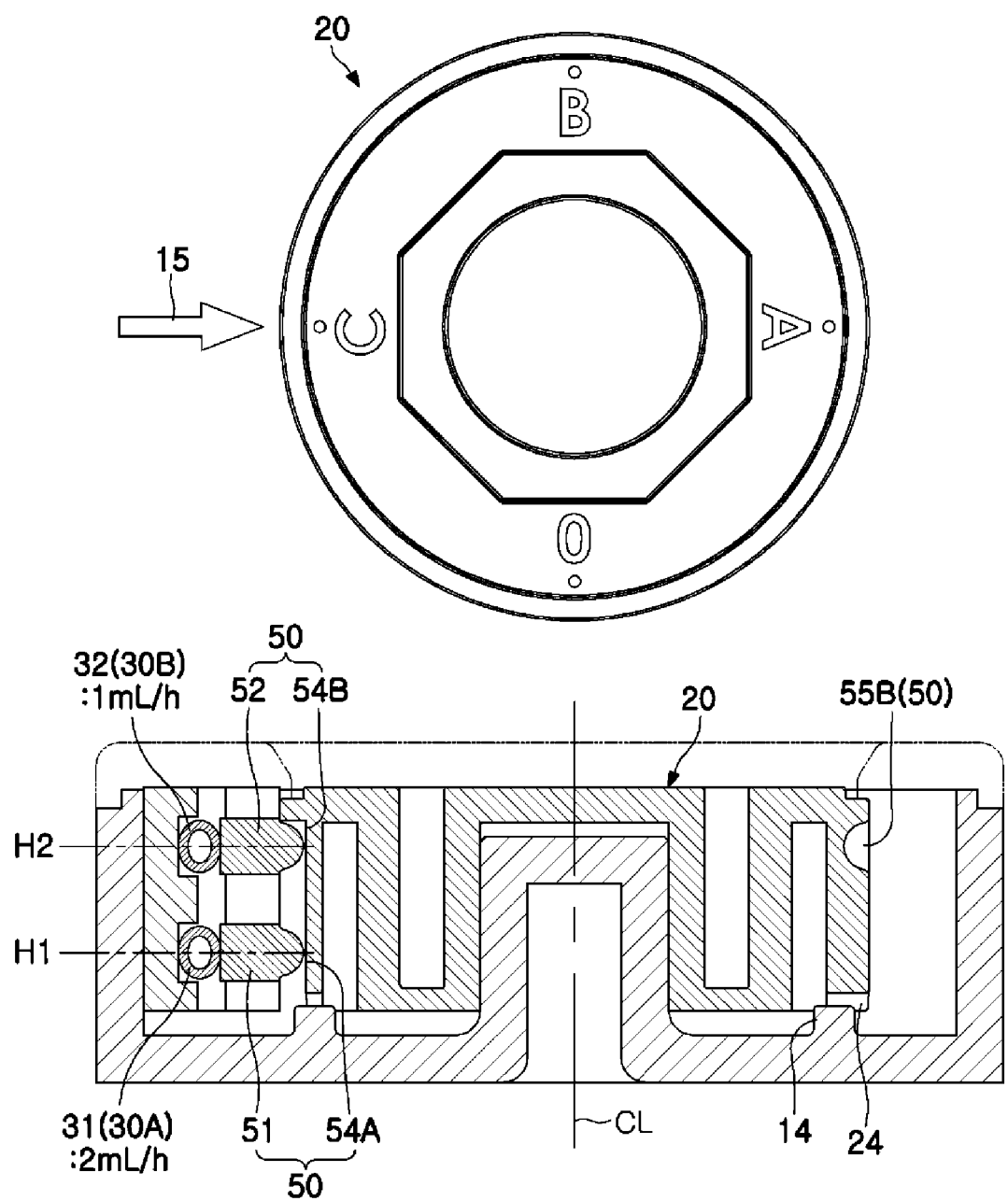
FIGS. 8 to 11 are views showing whether medicinal fluid lines are opened or closed in accordance with rotational angles of the operation knob of the medicinal fluid flow rate control apparatus according to the first embodiment of the present invention.
Figure 9:
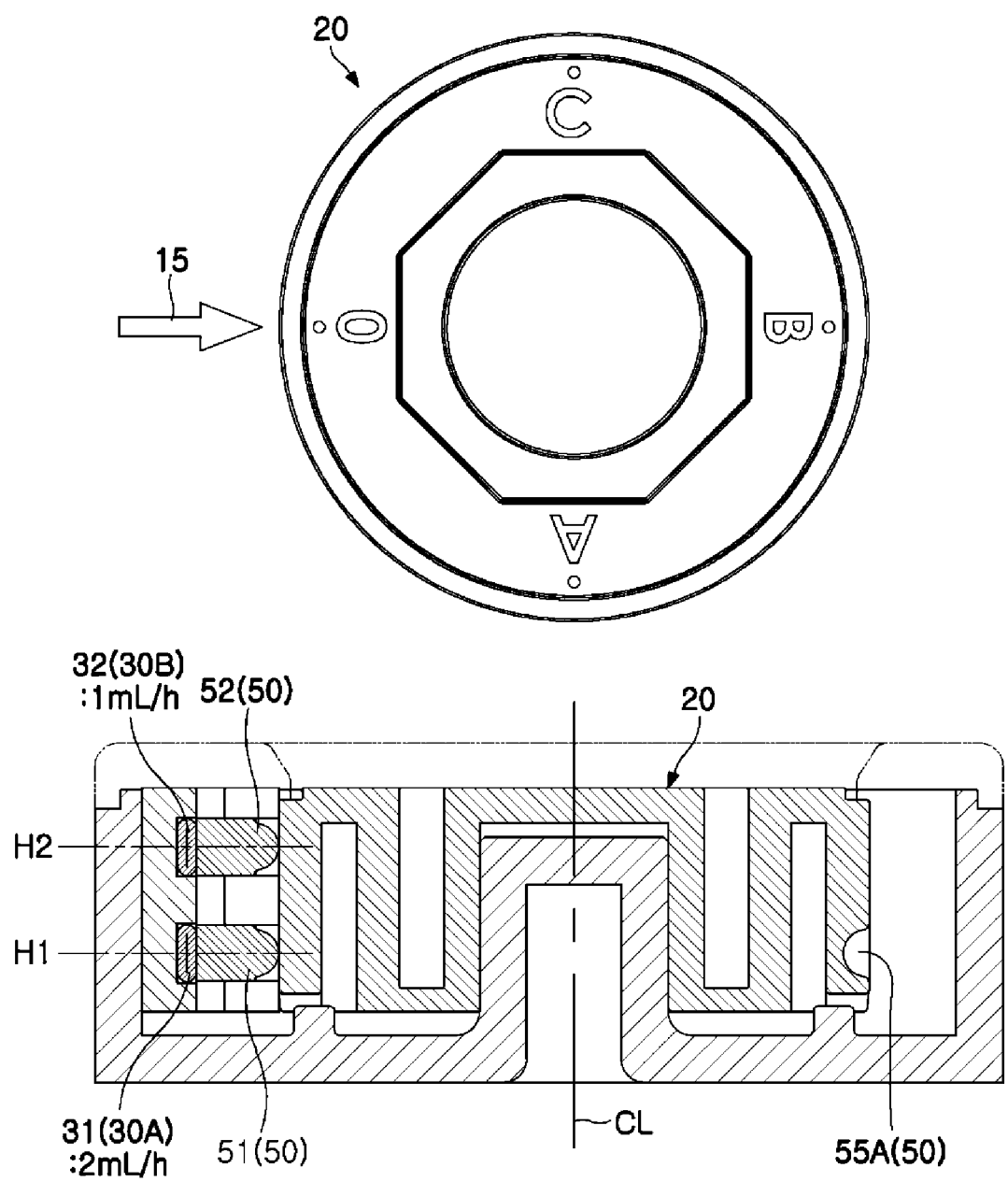

As shown in FIG. 8, when the operation knob 20 is turned clockwise by 90 degrees (by 90 degrees counterclockwise, depending on the arrangement of the recessions) when seen from above, with the spring plates 51 and 52 aligned with the first recessions 54A and 54B at the first and second heights H1 and H2 in the same vertical same, the spring plates 51 and 52 are both convexly bent toward the tubes 31 and 32 in contact with the outer side of the operation knob 20, as shown in FIG. 9, so the tubes 31 and 32 are both pressed and blocked by the spring plates 51 and 52, which is an off-mode (0 mL/h) in which a medicinal fluid is not discharged from the converging pipe 66. Obviously, the locking projection 14 is pulled out of a locking groove 24 and fitted into the next locking groove 24 while the operation knob 20 is turned by 90 degrees, whereby the position of the operation knob 20 is determined.

Figure 10:
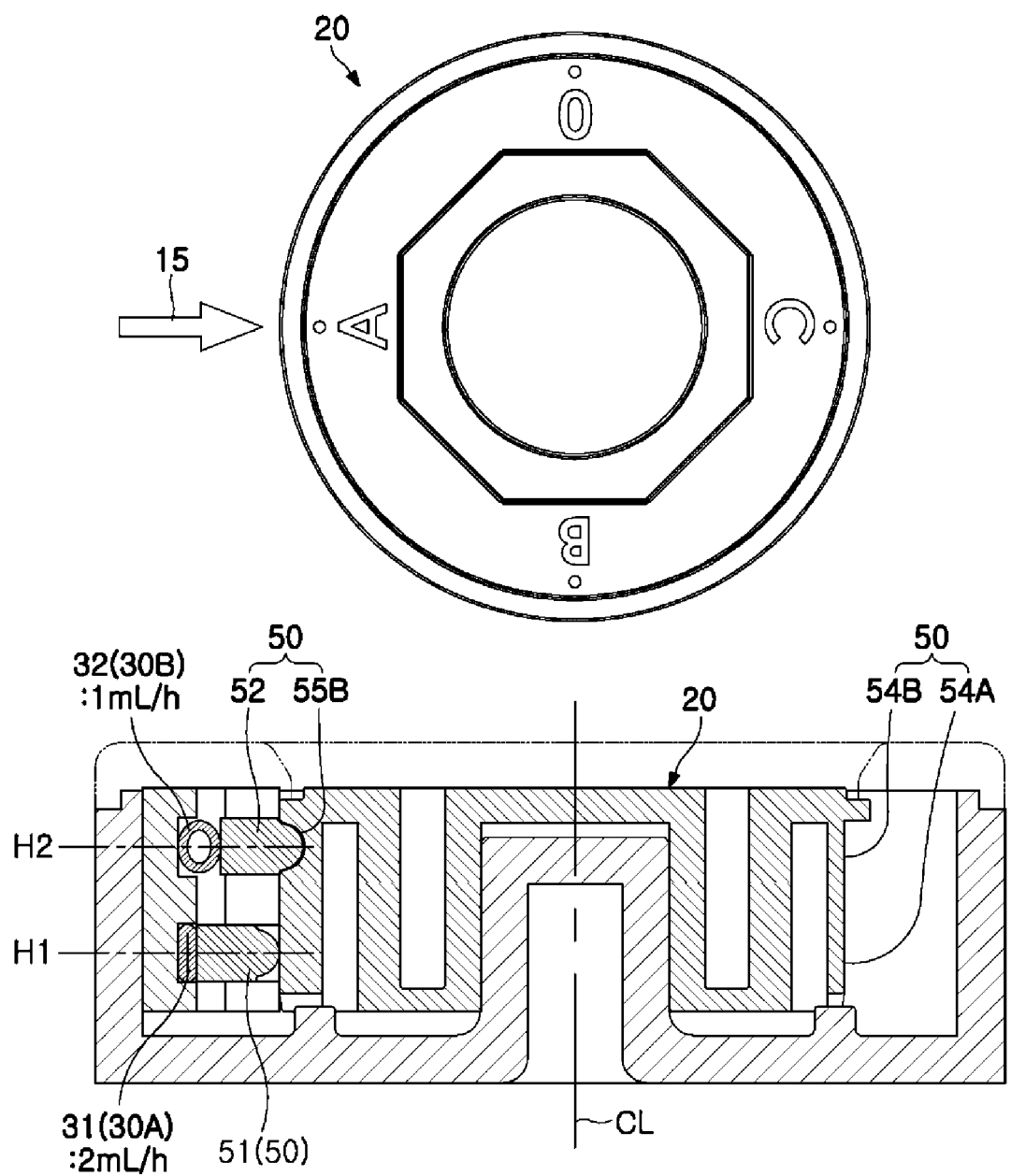

Next, when the operation knob 20 is further turned clockwise by 90 degrees when seen from above, as shown in FIG. 10, the spring plate 51 at the first height H1 remains bent and the tube 31 at the first height H1 remains pressed and blocked by the spring plate 51 at the first height H1, whereas the spring plate 52 at the second height H2 is restored into the initial state by moving into the second recession 55B at the second height H2 and the tube 32 pressed by the spring plate 52 at the second height H2 is opened, so a medicinal fluid is discharged at 1 mL/h from the converging pipe 66.

Figure 11:
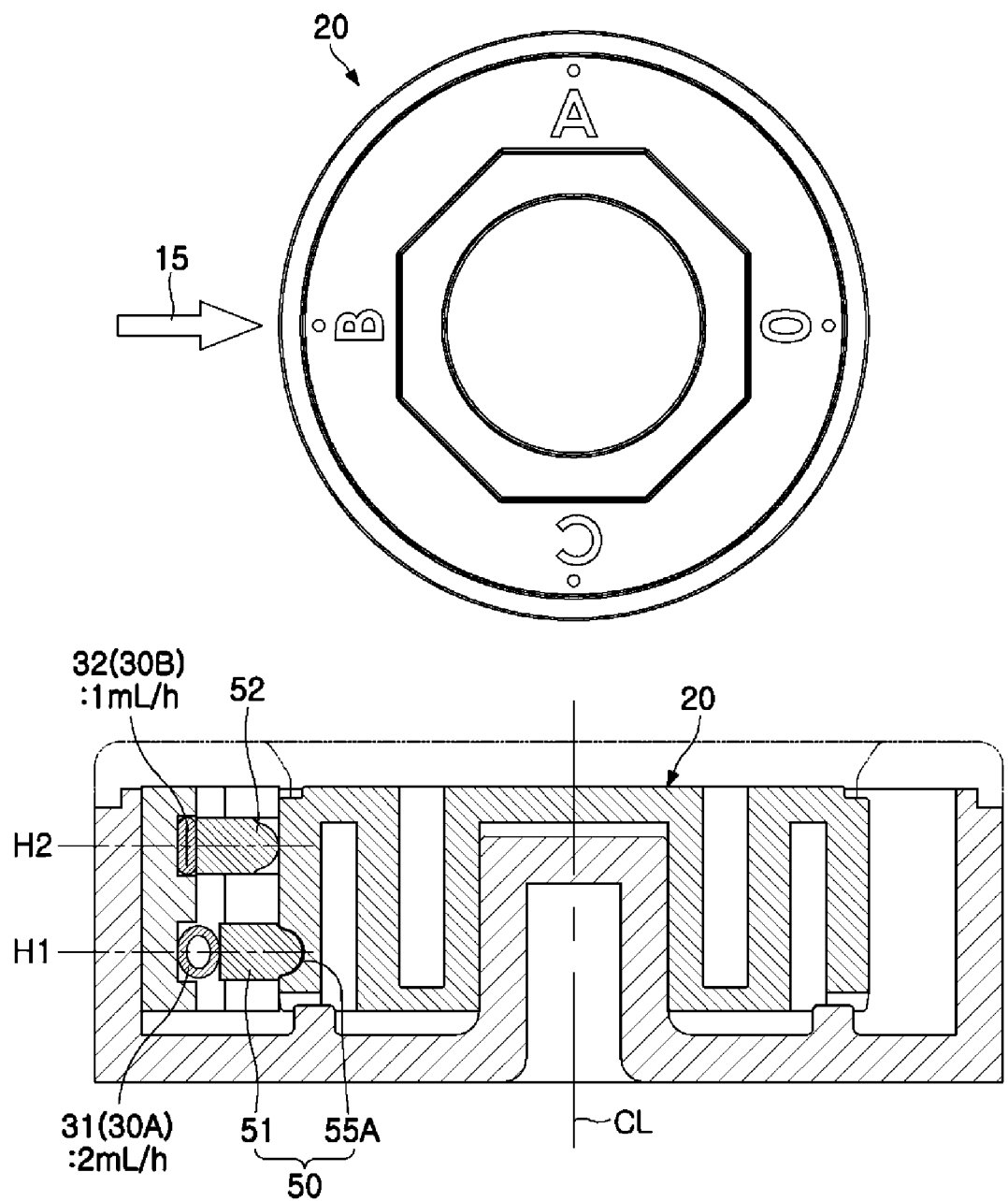

Next, when the operation knob 20 is further turned by 90 degrees when seen from above, as shown in FIG. 11, the spring plate 51 at the first height H1 is restored into the initial state by moving into the second recession 55A at the first height H1 and the tube 31 pressed by the spring plate 51 at the first height H1 is opened, whereas the spring plate 52 at the second height H2 comes in contact with the outer side of the operation knob 20 and is bent toward the tube 32 at the second height H2 and the tube 32 at the second height H2 is pressed and blocked by the spring plate 52 at the second height h2, so the medicinal fluid is discharged at 2 mL/h from the converging pipe 66.

When the operation knob 20 is further turned counterclockwise by 90 degrees to make one revolution when seen from above, as shown in FIG. 8, the spring plate 51 remains in the initial state by moving into the first recession 54A at the first height H1 and the tube 31 released from the spring plate 51 at the first height H1 remains open, whereas the spring plate 52 at the second height H2 is restored into the initial state by moving into the first recession 54B at the second height H2 and the tube 32 at the second height H2 is opened by being released from the spring plate 52 at the second height H2, so the medicinal fluid is discharged at 3 mL/h from the converging pipe 66.

This operation is briefly shown in the following Table 1.

TABLE 1

| | Medicinal fluid delivery line (30A) of 2 mL/h | Medicinal fluid delivery line (30B) of 1 mL/h |
|---|---|---|
| 0 mL/h | X | X |
| 1 mL/h | X | ○ |
| 2 mL/h | ○ | X |
| 3 mL/h | ○ | ○ |

○: Open
X: Blocked

The medicinal fluid flow rate control apparatus that is operated, as described above, in accordance with the first embodiment of the present invention can be used as follows.

Patients who have undergone an operation feel different degrees of pain, depending on the type of operations or on individual differences, but in most cases, they feel a severe pain in the early stage after an operation, and the pain gradually decreases as time passes and is considerably attenuated after about three days. Accordingly, when a medicinal fluid is given for pain management to a patient who is in the early stage after the operation, the mode with both of the medicinal fluid delivery lines 30A and 30B, as shown in FIG. 8, is selected, and then as the pain attenuates, the mode can be changed such that the dosage of the medicinal fluid is decreased step by step.

Terminal cancer patients feel more pain, as time passes, in contrast to patients who have undergone an operation, so it is possible to increase the dosage of a medicinal fluid step by step.

Meanwhile, according to the medicinal fluid flow rate control apparatus according to the first embodiment of the present invention, since the tubes 31 and 32 and the spring plates 51 and 52 are concentrated at a side of the operation knob 20 without distributing at several positions, it is possible to further simplify the arrangement structure of the medicinal fluid delivery lines 30A and 30B and the installation structure of the spring plates 51 and 52, which is advantageous in terms of a compact size, improvement of assembly, and maintenance.

Reference numeral '15', which was not stated above indicates an indicator. The indicator 15 is disposed at a side of the knob hole 12 on the top of the second case 10B to be seen from the outside and the flow speed (0 mL/h, 1 mL/h, 2 mL/h, and 3 mL/h) of the medicinal fluid or the modes 0, A, B, and C that are indicated by the indicator 15 are shown on the top of the operation knob 20 around the coupling groove 22.

[Medicinal Fluid Flow Rate Control Apparatus According to Second Embodiment]

A medicinal fluid flow rate control apparatus according to the second embodiment of the present invention is shown in FIGS. 12 to 20.

The medicinal fluid flow rate control apparatus according to the second embodiment of the present invention adjusts the flow rate of a medicinal fluid by selectively opening and shutting two medicinal fluid delivery lines, so it is different in that it has a 3-channel structure. However, other configurations and operations are similar to the medicinal fluid flow rate control apparatus having a 2-channel structure according to the first embodiment. This difference is as follows.

The medicinal fluid flow control apparatus according to the second embodiment of the present invention, for a 3-channel structure, includes three medicinal fluid delivery lines 130A, 130B, and 130C, spring plates 151, 152, and 153, flow rate control pipes 162A, 162B, and 162C, and twelve recessions.

The medicinal fluid delivery lines 130A, 130B, and 130C have tubes 131, 132, and 133 positioned at different first, second, and third heights H11, H12, and H13 at a side of an operation knob 120. Obviously, the tubes 131, 132, and 133 at the first, second, and third heights H11, H12, and H13 are separately seated in three tube seats of a tube support member 140, and ends of the medicinal fluid delivery lines 130A, 130B, 130C are connected to the flow rate control pipes 162A, 162B, and 162C and diverging pipes 167.

Spring plates 151, 152, and 153 are positioned at heights corresponding to the heights H11, H12, and H13 of the tubes 131, 132, and 133, between the operation knob 120 and the vertically arranged tubes 131, 132, and 133.

Four recessions are formed at each of the heights H11, H12, and H13 corresponding to the spring plates 151, 152, and 153 on and around the operation knob 120 and selectively press or release the tubes 131, 132, and 133 in cooperation with the spring plates 151, 152, and 153 to open or block all of the medicinal fluid delivery lines 130A, 130B, and 130C or open only some of the medicinal fluid delivery lines 130A, 130B, and 130C.

When the medicinal fluid flow rate control apparatus according to the second embodiment of the present invention is configured such that a medicinal fluid flows at 4 mL/h through the flow rate control pipe 162A connected to the medicinal fluid delivery line 130A having the tube 131 at the first height H11, a medicinal fluid flows at 2 mL/h through the flow rate control pipe 162B connected to the medicinal fluid delivery line 130B having the tube 132 at the second height H12, and a medicinal fluid flows at 1 mL/h through the flow rate control pipe 162C connected to the medicinal fluid delivery line 130C having the tube 133 at the third height H13, thus it is possible to adjust the amount of a medicinal fluid that is injected into a subject by selecting one of a total of eight modes.

Figure 13:
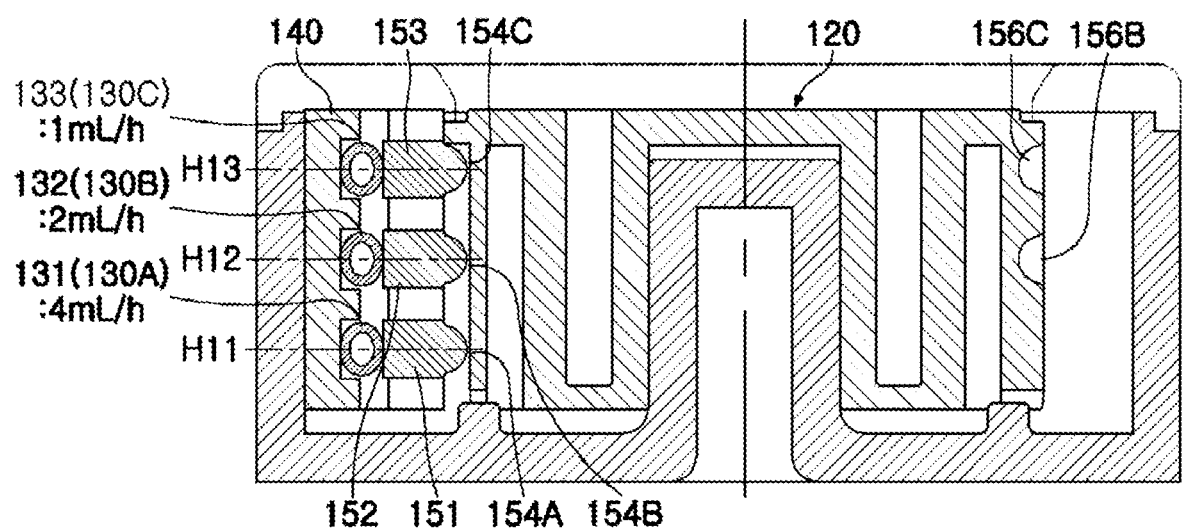
FIGS. 13 to 20 are views showing whether medicinal fluid lines are opened or closed in accordance with rotational angles of the operation knob of the medicinal fluid flow rate control apparatus according to the second embodiment of the present invention.
Figure 14:
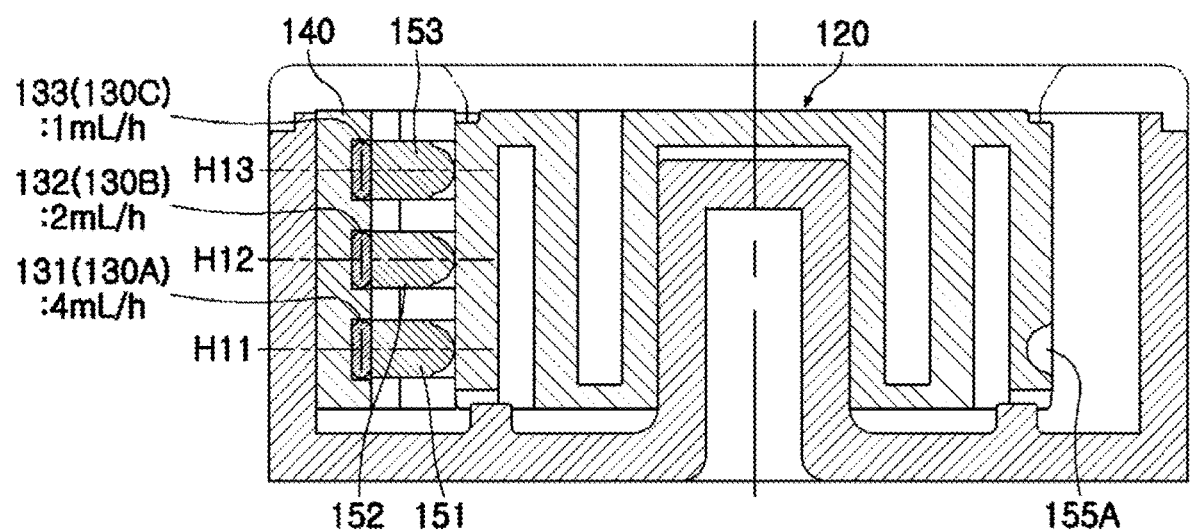

As shown in FIG. 13, when the operation knob 120 is turned counterclockwise by 45 degrees (by 45 degrees clockwise, depending on the arrangement of the recessions) when seen from above, with the spring plates 151, 152, and 153 aligned with the first recessions 154A, 154B, and 154C at the first to third heights H11, H12, and H13 in the same vertical line, the spring plates 151, 152, and 153 are all bent convexly toward the tubes 131, 132, and 133 in contact with the outer side of the operation knob 120, as shown in FIG. 14, so the tubes 131, 132, and 133 are all pressed and blocked by the spring plates 151, 152, and 153. This configuration is an off-mode (0 mL/h).

Figure 15:
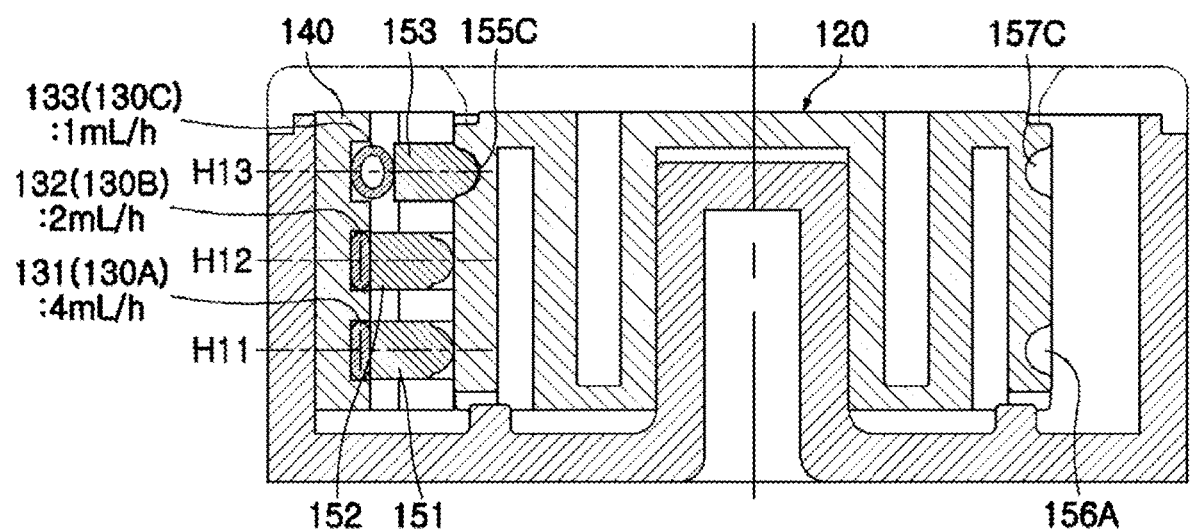

Next, when the operation knob 120 is further turned by 45 degrees, as shown in FIG. 15, the spring plates 151 and 152 at the first and second heights H11 and H12 come in contact with the outer side of the operation knob 120 and the spring plate 153 at the third height H13 moves into the second recession 155C at the third height H13. Accordingly, the tubes 131 and 132 at the first and second heights H11 and H12 are blocked and the tube 133 at the third height H13 is pressed by the spring plate 153 at the third height H13 is released, as the spring plate 153 at the third height H12 is restored into the initial state. Accordingly, a medicinal fluid is discharged at 1 mL/h from the converging pipe 166.

Figure 16:
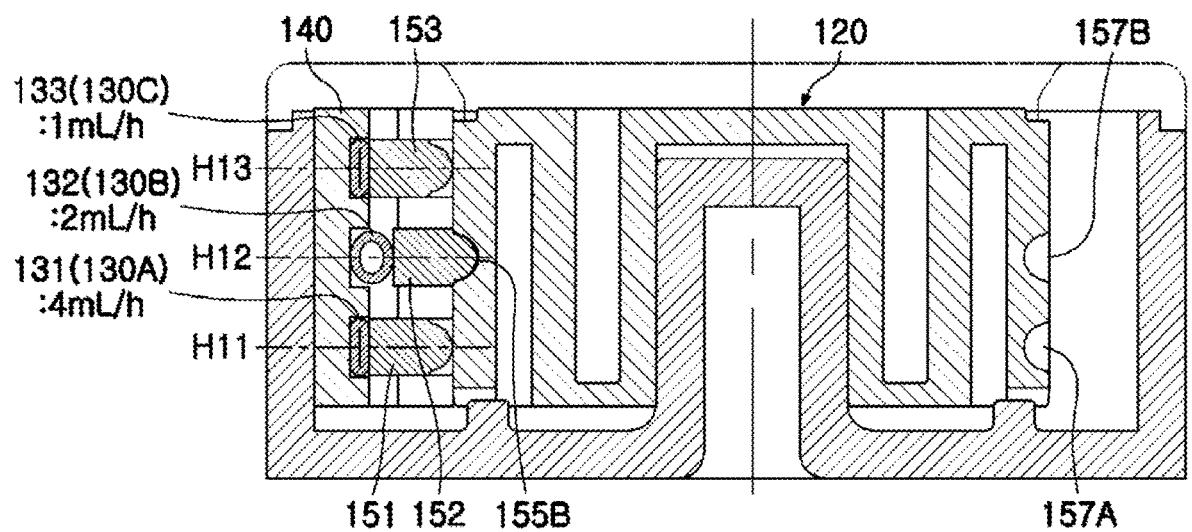

Next, when the operation knob 120 is further turned, as shown in FIG. 16, the spring plates 151 and 153 at the first and third heights H11 and H13 come in contact with the outer side of the operation knob 120 and the spring plate 152 at the second height H12 moves into the second recession 155B at the second height H12. Accordingly, the tubes 131 and 133 at the first and third heights H11 and H13 are blocked and the tube 132 at the second height H12 is opened, so the medicinal fluid is discharged at 2 mL/h from the converging pipe 166.

Figure 17:
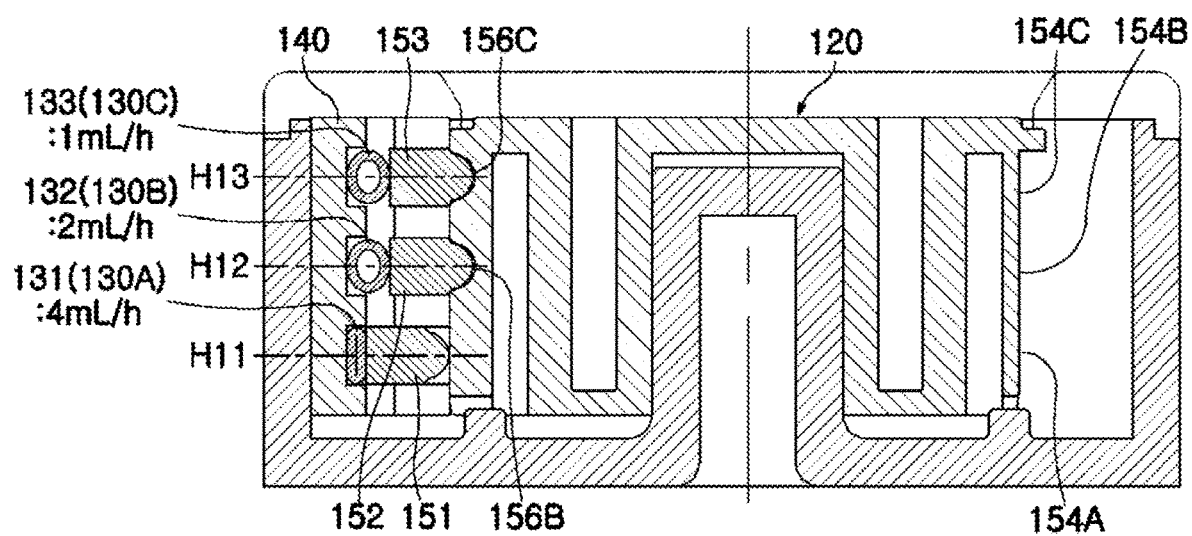

Next, when the operation knob 120 is further turned by 45 degrees, as shown in FIG. 17, the spring plate 151 at the first height H11 comes in contact with the outer side of the operation knob 120 and the spring plates 152 and 153 at the second and third heights H12 and H13 move into the third recessions 156B and 156C at the second and third heights H12 and H13. Accordingly, the tube 131 at the first height H11 is blocked and the tubes 132 and 133 at the second and third heights H12 and H13 are opened, so the medicinal fluid is discharged at 3 mL/h from the converging pipe 166.

Figure 18:
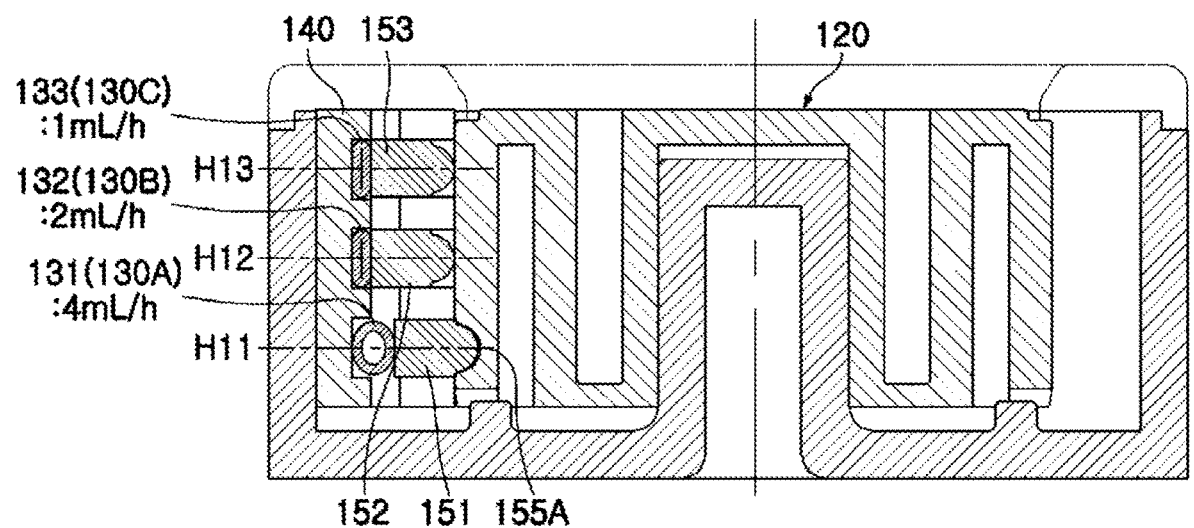

Next, when the operation knob 120 is further turned by 45 degrees, as shown in FIG. 18, the spring plates 152 and 153 at the second and third heights H12 and H13 come in contact with the outer side of the operation knob 120 and the spring plate 151 at the first height H11 moves into the second recession 155A at the first height H11. Accordingly, the tubes 132 and 133 at the second and third heights H12 and H13 are blocked and the tube 131 at the first height H11 is opened, so the medicinal fluid is discharged at 4 mL/h from the converging pipe 166.

Figure 19:
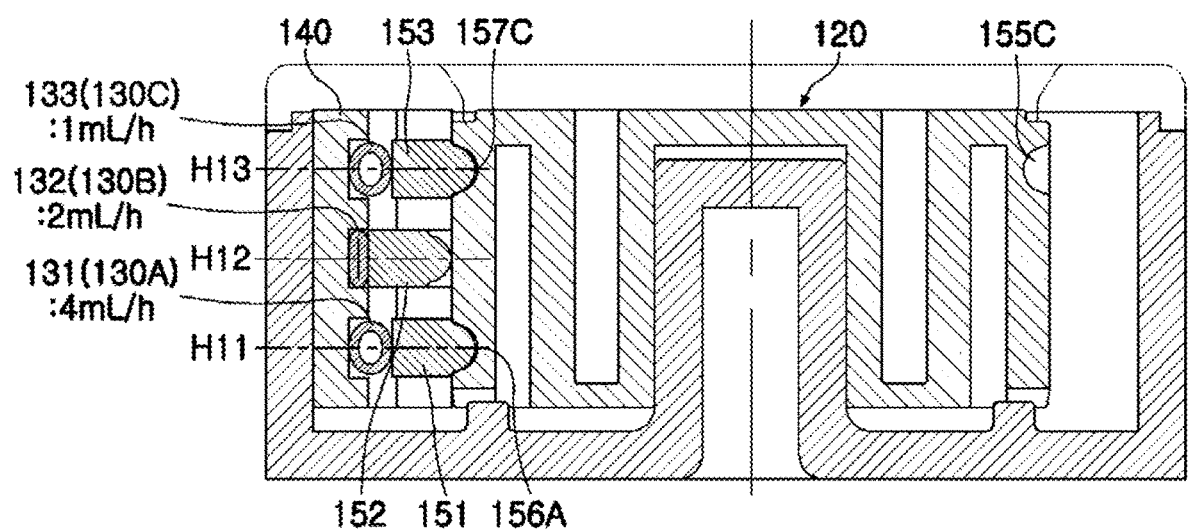

Next, when the operation knob 120 is further turned by 45 degrees, as shown in FIG. 19, the spring plate 152 at the second height H12 comes in contact with the outer side of the operation knob 120 and the spring plates 151 and 153 at the first and third heights H11 and H13 move into the third recession 156A at the first height H11 and the fourth recession 157C at the third height H13. Accordingly, the tube 132 at the second height H12 is blocked and the tubes 131 and 133 at the first and third heights H11 and H13 are opened, so the medicinal fluid is discharged at 5 mL/h from the converging pipe 166.

Figure 20:
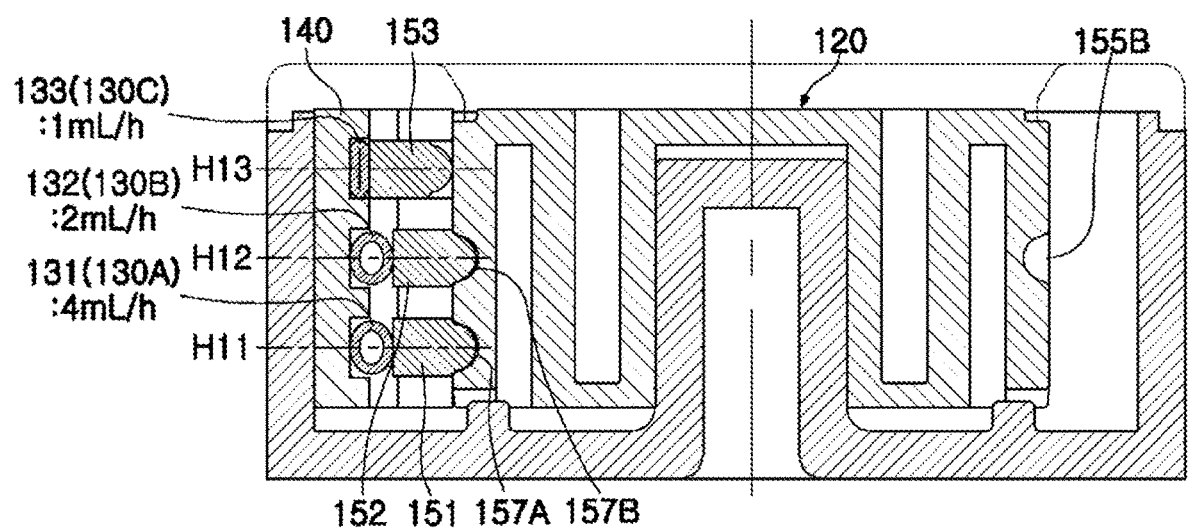

Next, when the operation knob 120 is further turned by 45 degrees, as shown in FIG. 20, the spring plate 153 at the third height H13 comes in contact with the outer side of the operation knob 120 and the spring plates 151 and 152 at the first and second heights H11 and H12 move into the fourth recessions 157A and 157B at the first and second heights H11 and H12. Accordingly, the tube 133 at the third height H13 is blocked and the tubes 131 and 132 at the first and second heights H11 and H12 are opened, so the medicinal fluid is discharged at 6 mL/h from the converging pipe 166.

Next, when the operation knob 120 is further turned by 45 to make one revolution, as shown in FIG. 13, the spring plates 151, 152, and 153 move into the first recessions 154A, 154B, and 154C, respectively. Accordingly, the tubes 131, 132, and 133 are all opened, so the medicinal fluid is discharged at 7 mL/h from the converging pipe 166.

The operation of the medicinal fluid flow rate control apparatus according to the second embodiment of the present invention is briefly shown in the following Table 2.

TABLE 2

| | Medicinal fluid delivery line (130A) of 4 mL/h | Medicinal fluid delivery line (130B) of 2 mL/h | Medicinal fluid delivery line (130C) of 1 mL/h |
|---|---|---|---|
| 0 mL/h | X | X | X |
| 1 mL/h | X | X | ○ |
| 2 mL/h | X | ○ | X |
| 3 mL/h | X | ○ | ○ |
| 4 mL/h | ○ | X | X |
| 5 mL/h | ○ | X | ○ |
| 6 mL/h | ○ | ○ | X |
| 7 mL/h | ○ | ○ | ○ |

○: Opened
X: Blocked

Figure 12:
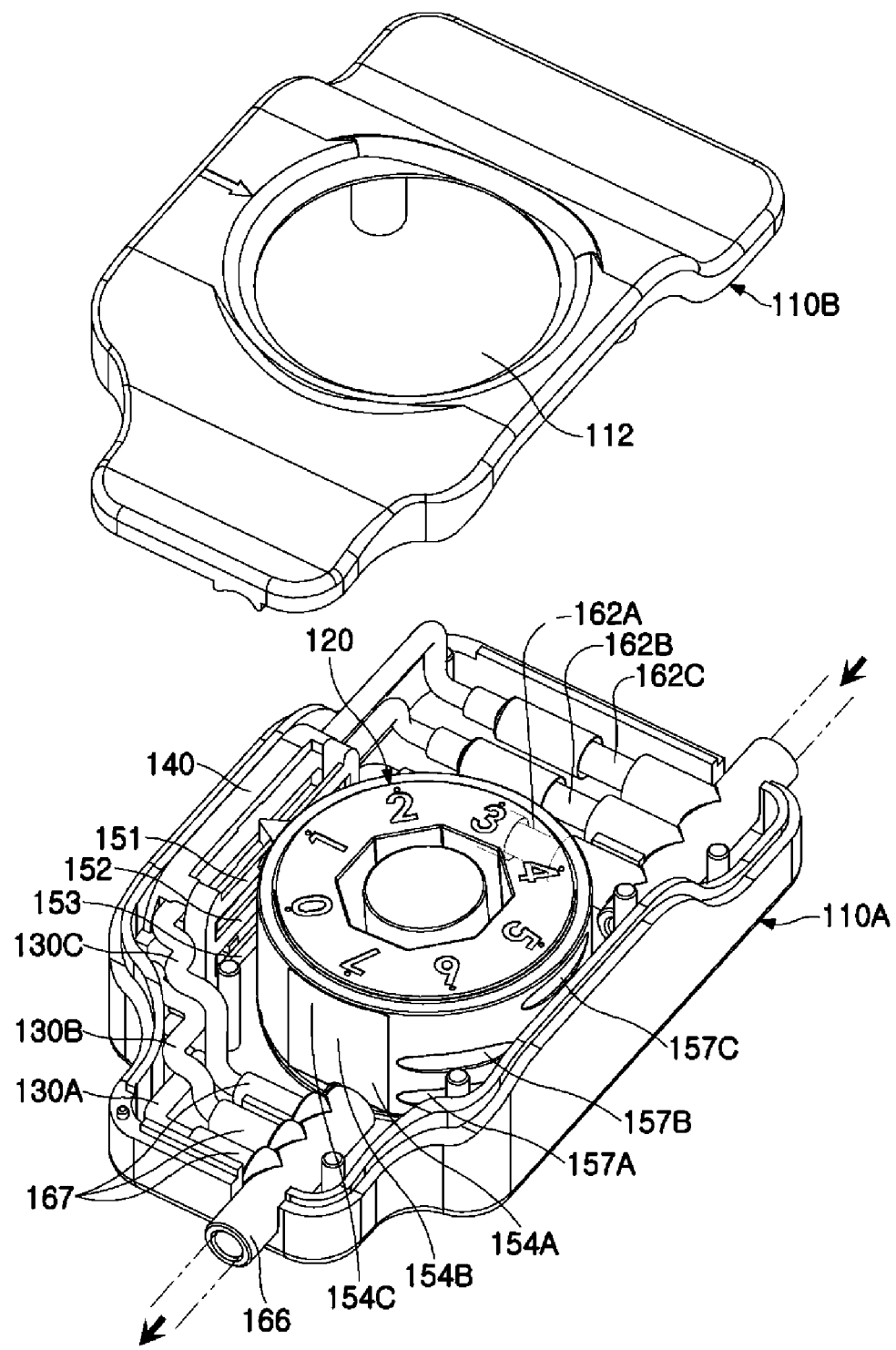
FIG. 12 is an exploded perspective view showing a medicinal fluid flow rate control apparatus according to a second embodiment of the present invention.

Reference numeral '110A' and '110B' shown in FIG. 12, but not stated above, indicate a first case and a second case that are the lower and upper parts, respectively, and are combined, and Reference numeral '112' indicates an operation knob.

[Medicinal Fluid Flow Rate Control Apparatus of Third Embodiment]

Figure 21:
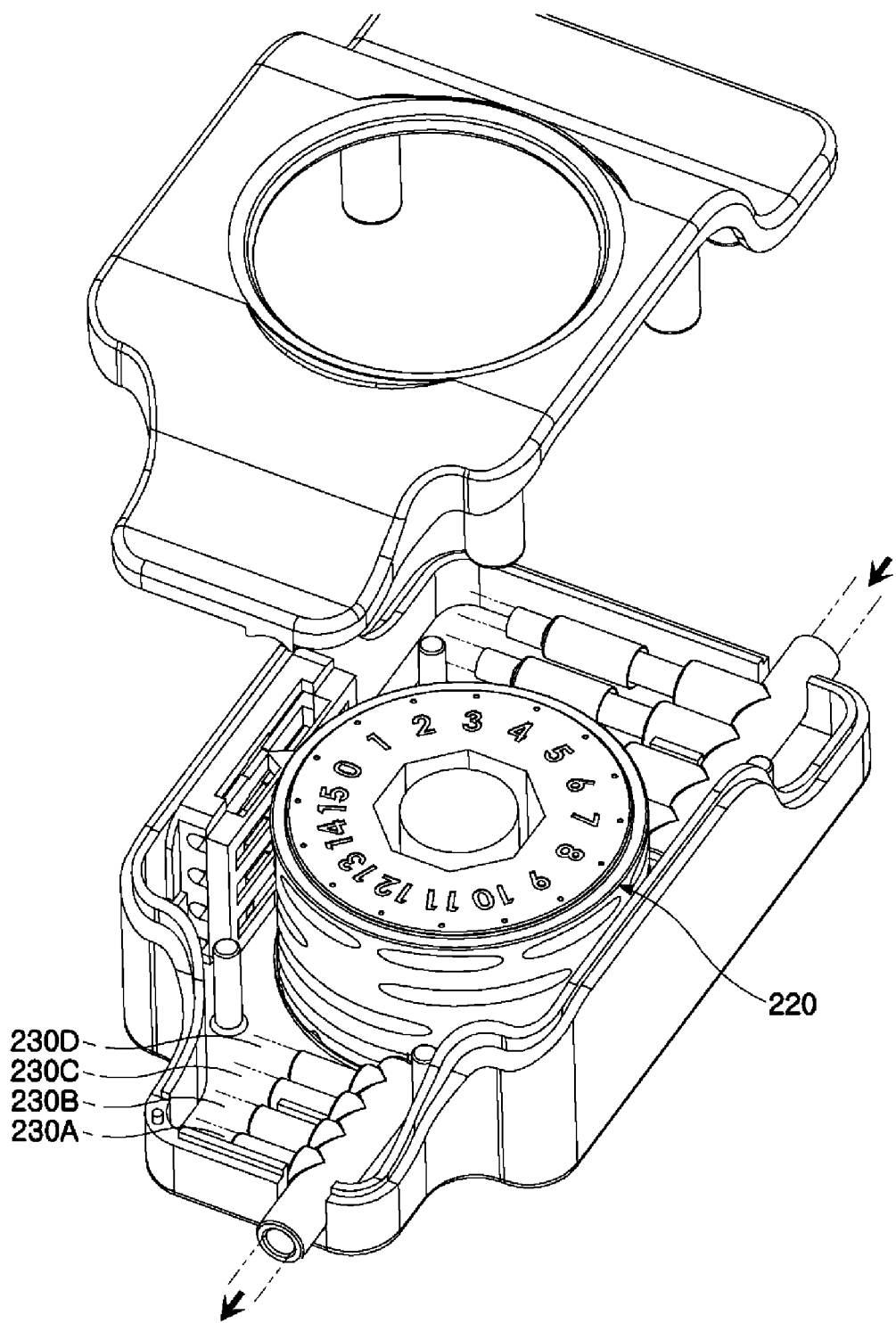
FIG. 21 is an exploded perspective view showing a medicinal fluid flow rate control apparatus according to a third embodiment of the present invention.

A medicinal fluid flow rate control apparatus according to the third embodiment of the present invention is shown in FIG. 21. As shown in FIG. 21, the medicinal fluid flow rate control apparatus according to the third embodiment of the present invention is different in that it has a 4-channel structure. However, other configurations and operations are similar to the medicinal fluid flow rate control apparatus having a 2-channel structure (or 3-channel structure) according to the first embodiment (or second embodiment).

When the medicinal fluid flow rate control apparatus according to the fourth embodiment of the present invention is configured such that a medicinal fluid flows at 8 mL/h through a flow rate control pipe connected to a medicinal fluid delivery line 230A having a tube at a first height, the medicinal fluid flows at 4 mL/h through a flow rate control pipe connected to the medicinal fluid delivery line 230B having a tube at a second height, the medicinal fluid flows at 2 mL/h through a flow rate control pipe connected to a medicinal fluid delivery line 230C having a tube at the second height, and the medicinal fluid flows at 1 mL/h through a flow rate control pipe connected to the medicinal fluid delivery line 230D having a tube at a fourth height, it is possible to adjust the amount of a medicinal fluid that is injected into a subject by selecting one of a total of sixteen modes while an operation knob 220 is turned by 22.5 degrees at each time.

TABLE 3

| | Medicinal fluid delivery line of 8 mL/h | Medicinal fluid delivery line of 4 mL/h | Medicinal fluid delivery line of 2 mL/h | Medicinal fluid delivery line of 1 mL/h |
|---|---|---|---|---|
| 0 mL/h | X | X | X | X |
| 1 mL/h | X | X | X | ○ |
| 2 mL/h | X | X | ○ | X |
| 3 mL/h | X | X | ○ | ○ |
| 4 mL/h | X | ○ | X | X |
| 5 mL/h | X | ○ | X | ○ |
| 6 mL/h | X | ○ | ○ | X |
| 7 mL/h | X | ○ | ○ | ○ |
| 8 mL/h | ○ | X | X | X |
| 9 mL/h | ○ | X | X | ○ |
| 10 mL/h | ○ | X | ○ | X |
| 11 mL/h | ○ | X | ○ | ○ |
| 12 mL/h | ○ | ○ | X | X |
| 13 mL/h | ○ | ○ | X | ○ |
| 14 mL/h | ○ | ○ | ○ | X |
| 15 mL/h | ○ | ○ | ○ | ○ |

○: Opened
X: Blocked

Although embodiments of medicinal fluid flow rate control apparatuses having 2-channel, 3-channel, and 4-channel structures of the present invention have been described above, a medicinal fluid flow rate control apparatus of the present invention is not limited thereto, and the number of the medicinal fluid delivery lines may be appropriately increased and the numbers of the spring plates, flow rate control pipes, and diverging pipes may be appropriately increased to achieve a 5-channel structure. Further, the number of the recessions arranged at predetermined heights, respectively, may also be appropriately increased and the arrangement of the recessions at the heights may also be appropriately changed.

Further, although the flow speeds of a medicinal fluid in the flow rate control pipes are set at 1 mL/h and 2 mL/h, or 1 mL/h, 2 mL/h, and 4 mL/h in the medicinal fluid flow rate control apparatuses of the present invention, the flow speeds may be changed to 0.5 mL/h and 1.0 mL/h, or 0.5 mL/h, 1.0 mL/h, and 2 mL/h.

[Example of Medicinal Fluid Injector]

Figure 22:
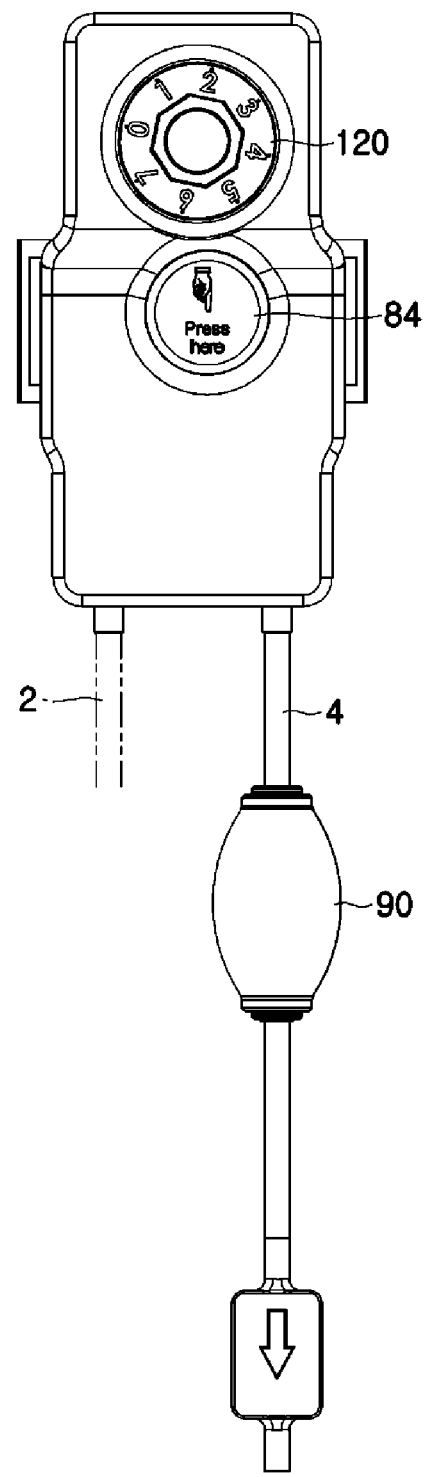
FIGS. 22 to 24 are plan views showing an example of a medicinal fluid injector according to the present invention.
Figure 23:
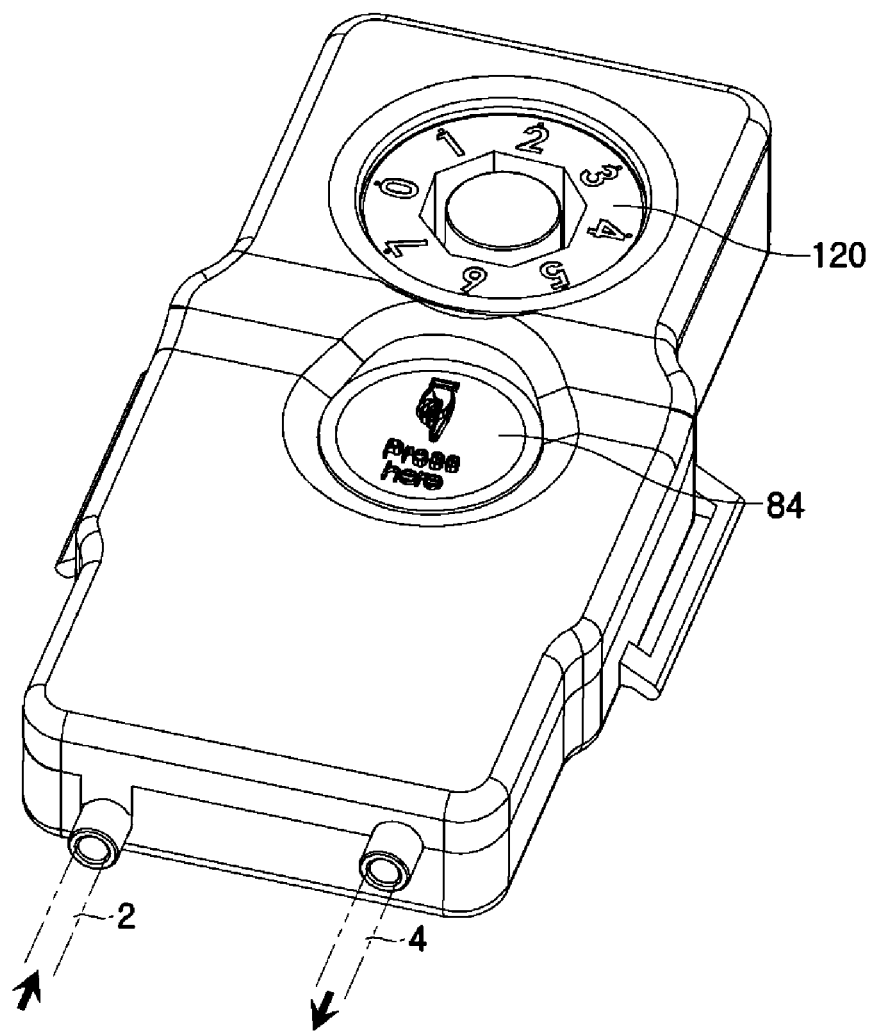
Figure 24:
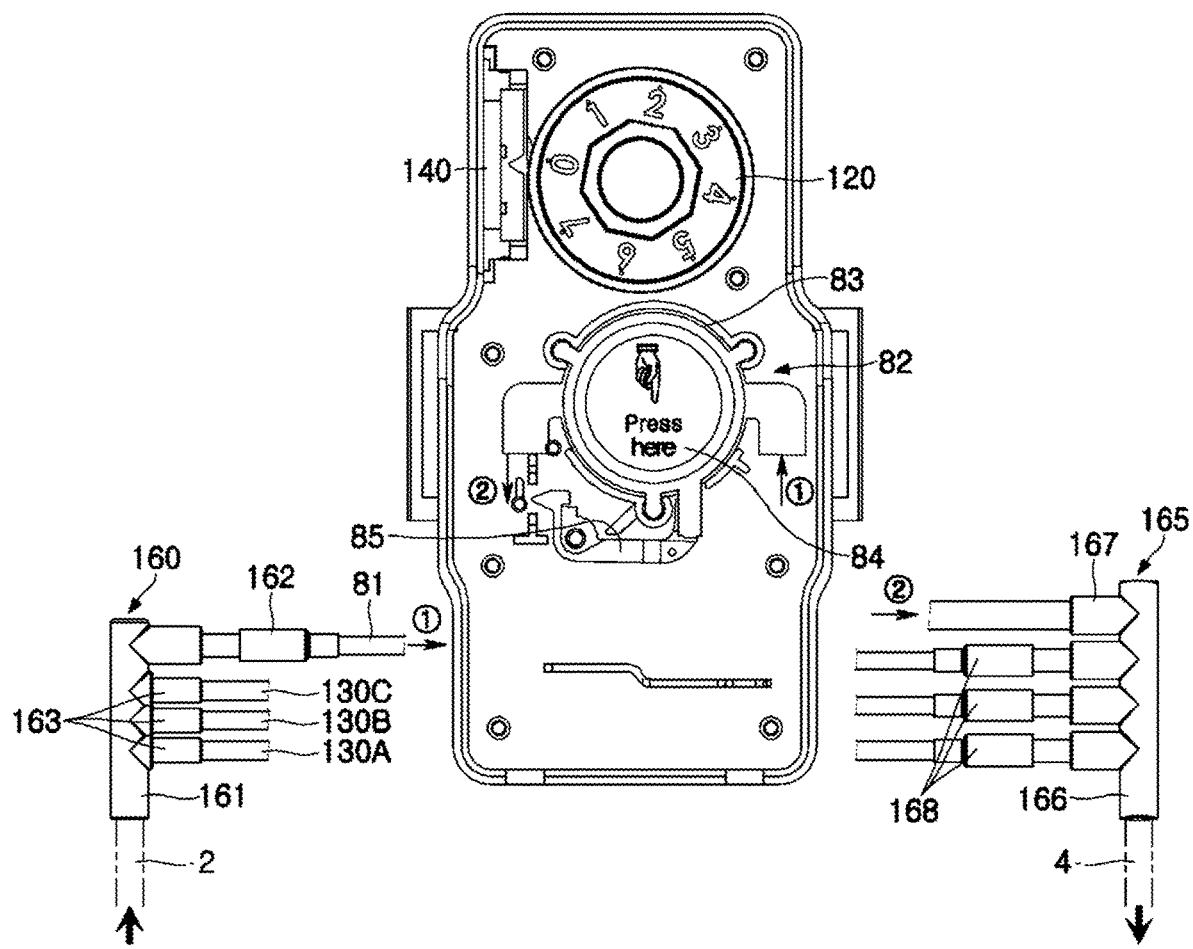

An example of a medicinal fluid injector including a medicinal fluid flow rate control apparatus of the present invention is shown in FIGS. 22 to 24.

As shown in FIGS. 22 to 24, the medicinal fluid flow rate control apparatus (see reference numerals 120, 130A, 130B, 130C, 140, etc.) having a 3-channel structure for adjusting the amount of a medicinal fluid that is continuously injected into a subject by a user and a bolus apparatus (see reference numerals 81, 82, etc.) for instantaneously increasing the amount of a medicinal fluid that is injected into a subject by a user are applied to the example of a medicinal fluid injector. Obviously, medicinal fluid flow rate control apparatuses having not a 3-channel structure, but a 2-channel structure or 4- or more-channel structures may be used.

The medicinal fluid flow rate control apparatus and the bolus apparatus are installed in a case including a first case that is the lower part and a second case that is the upper part.

The medicinal fluid flow rate control apparatus is the same as or similar to the medicinal fluid flow rate control apparatus having a 3-channel structure according to the second embodiment. Accordingly, in the following description of the medicinal fluid flow rate control apparatus, the same components as those of the medicinal fluid flow rate control apparatus according to the second embodiment are given the same reference numerals.

The medicinal fluid flow rate control apparatus includes an operation knob 120, three first medicinal fluid delivery lines 130A, 130B, and 130C, a tube support member 140, and a first pipe switch (spring plates and recessions). When the operation knob 120 is turned, the first medicinal fluid delivery lines 130A, 130B, and 130C supported by the tube support member 140 are selectively opened and blocked by the first pipe switch, depending on the rotational angle of the operation knob 120. These components are substantially the same as those of the medicinal fluid flow rate control apparatus according to the second embodiment, so they are not described in detail.

The bolus apparatus includes a second medicinal fluid delivery line 81 and a medicinal fluid pumping unit 82 disposed in the second medicinal fluid delivery line 81, keeping a medicinal fluid from the second medicinal fluid delivery line 81, and pumping the kept medicinal fluid to an exit.

The medicinal fluid pumping unit 82 includes a bolus bag 83 keeping the medicinal fluid from the second medicinal fluid delivery line 81, a push button 84 applying an external force to the bolus bag 83 when being pressed, and a second pipe switch 85 opening or blocking the second medicinal fluid delivery line 81 when the push button 84 is operated. When the push button 84 is pressed, the medicinal fluid kept in the bolus bag 83 is pumped to the exit. When the push button 84 is pressed, the second pipe switch 85 opens the second medicinal fluid delivery line 81, and when the push button 84 is released, the second pipe switch 85 blocks the second medicinal fluid delivery line 81. This configuration has been disclosed in Korean Patent No. 10-1126213, so it is not described in detail.

Reference numeral '160' indicates a medicinal fluid distributor, reference numeral '165' indicates a medicinal fluid converger, and reference numeral '90' indicates a medicinal fluid discharge maintainer.

The medicinal fluid distributor 160 may be composed of an inflow pipe 161, a flow rate control pipe 162 diverging from the inflow pipe 161, and three diverging pipes 163. In the medicinal fluid distributor 160, a medicinal fluid inflow hose 2 may be connected to the inflow pipe 161, a first end of the second medicinal fluid delivery line 81 may be connected to the flow rate control pipe 162, and first ends of the first medicinal fluid delivery lines 130A, 130B, and 130C may be connected to the diverging pipes 163, respectively.

The medicinal fluid converger 165 may be composed of a converging pipe 166, a diverging pipe 167 diverging from the converging pipe 166, and three flow rate control pipes 168. In the medicinal fluid converger 165, a medicinal fluid discharge hose 4 may be connected to the converging pipe 166, a second end of the second medicinal fluid delivery line 81 may be connected to the diverging pipe 167, and second ends of the first medicinal fluid delivery lines 130A, 130B, and 130C may be connected to the flow rate control pipes 168, respectively.

The medicinal fluid distributor 160 and the medicinal fluid converger 165 are different from those of the medicinal fluid flow rate control apparatus according to the second embodiment in that a medicinal fluid is distributed into the first medicinal fluid delivery lines 130A, 130B, and 130C and the second medicinal fluid delivery line 81, and the medicinal fluids discharged from the first medicinal fluid delivery lines 130A, 130B, and 130C and the second medicinal fluid delivery line 81 are converged, but the other configuration and operation are the same or similar.

The medicinal fluid discharge maintainer 90 is disposed in the medicinal fluid discharge hose 4 outside the case. The medicinal fluid discharge maintainer 80 temporarily keeps a medicinal fluid pumped from the second medicinal fluid delivery line 81 and continuously discharges the temporarily kept medicinal fluid to the medicinal fluid discharge hose 4, when the push button 84 is pressed. The medicinal fluid discharge maintainer 90 includes a balloon that is inflated by pressure of the medicinal fluid pumped from the bolus bag 83 and an anti-backflow unit that prevents backflow of a medicinal fluid that is discharged when the inflated balloon contracts. This component has been disclosed in Korean Patent No. 10-1126213, so it is not described in detail.

According to the example of a medicinal fluid injector, the medicinal fluid from the medicinal fluid inflow hose 2 is distributed by the medicinal fluid distributor 160 and flows into the first medicinal fluid delivery lines 130A, 130B, and 130C and the second medicinal fluid delivery line 81.

Unless the medicinal fluid flow rate control apparatus is set in the off-mode (0 mL/h), the medicinal fluid supplied into the first medicinal fluid delivery lines 130A, 130B, and 130C flows into the medicinal fluid converger 165 at a flow rate set by the medicinal fluid flow rate control apparatus. The medicinal fluid supplied into the second medicinal fluid delivery line 81 is kept in the bolus bag 83, but the second medicinal fluid delivery line 81 is opened only when the push button 84 is pressed, so the medicinal fluid kept in the bolus bag 83 is not discharged to the medicinal fluid converger 165. Accordingly, the medicinal fluid is continuously injected into a subject at the flow rate set by the medicinal fluid flow rate control apparatus.

In this state, when the push button 84 is pressed, the second medicinal fluid delivery line 81 is opened and the bolus bag 84 is pressed, so the medicinal fluid kept in the bolus bag 83 is pumped into the medicinal fluid converger 165. Accordingly, a large amount of medicinal fluid (the medicinal fluid from the first medicinal fluid delivery lines and the medicinal fluid from the bolus bag) is injected into a subject. Obviously, the medicinal fluid discharged from the medicinal fluid converger 165 in this process is temporarily kept in the medicinal fluid discharge maintainer 90 and continuously supplied to the subject.

[Another Example of Medicinal Fluid Injector]

Figure 25:
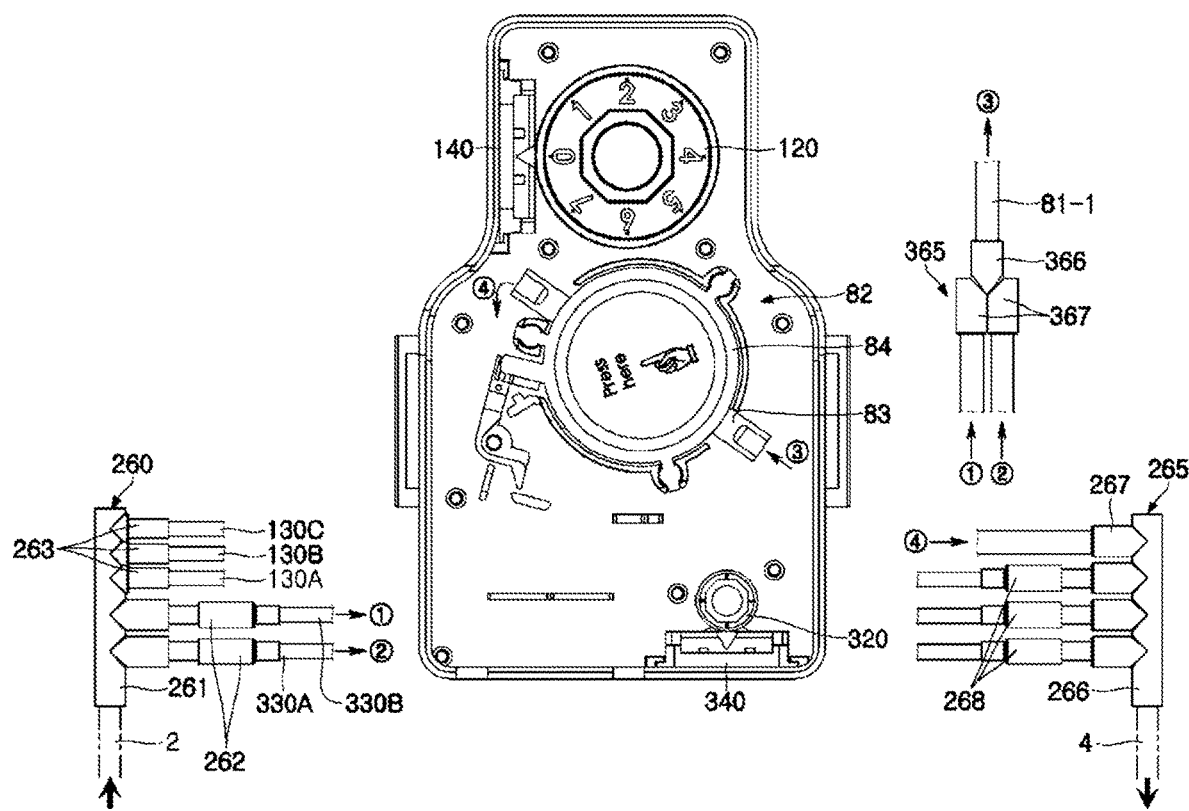
FIG. 25 is a view showing another example of a medicinal fluid injector according to the present invention.

Another example of a medicinal fluid injector including a medicinal fluid flow rate control apparatus according to the present invention is shown in FIG. 25. As shown in FIG. 25, another example of a medicinal fluid injector is different only in that it can adjust the flow rate of a medicinal fluid that is supplied to the bolus apparatus, as compared with the example of a medicinal fluid injector described above, but the other configuration and operation are all the same. This configuration is described hereafter. Further, for reference, the same components as those of the example of the medicinal fluid injector described above are given the same reference numerals.

The medicinal fluid injector of this example includes a first medicinal fluid flow rate control apparatus having a 3-channel structure for adjusting the amount of a medicinal fluid that is continuously injected into a subject by a user, a bolus apparatus that instantaneously increases the amount of a medicinal fluid that is injected into a subject by a user, and a second medicinal fluid flow rate control apparatus (see reference numerals 320A, 330A, 330B, 340A and etc.) having a 2-channel structure for adjusting the amount of a medicinal fluid that is supplied to the bolus apparatus by a user. Obviously, the second medicinal fluid flow rate control apparatus may have not the 2-channel structure, but a 3- or more-channel structure.

The first medicinal fluid flow rate control apparatus includes a first operation knob 120, three first medicinal fluid delivery lines 130A, 130B, and 130C, a first tube support member 140, and a first pipe switch.

The second medicinal fluid flow rate control apparatus includes a second operation knob 320, two second medicinal fluid delivery lines 330A and 330B, a second tube support member 340, and a second pipe switch (spring plates and recessions). When the second operation knob 320 is turned, the second medicinal fluid delivery lines 330A and 330B supported by the second tube support member 340 are selectively opened and blocked by the second pipe switch, depending on the rotational angle of the second operation knob 320. These components are the same as those of the medicinal fluid flow rate control apparatus according to the first embodiment, so they are not described in detail.

Reference numeral '260' indicates a medicinal fluid distributor, reference numeral '265' indicates a first medicinal fluid converger, and reference numeral '365' indicates a second medicinal fluid converger.

The medicinal fluid distributor 260 may composed of an inflow pipe 261, two flow rate control pipes 262 diverging from the inflow pipe 261, and three diverging pipes 263. In the medicinal fluid distributor 260, a medicinal fluid inflow hose 2 may be connected to the inflow pipe 261, first ends of the second medicinal fluid delivery lines 330A and 330B may be connected to the flow rate control pipes 262, respectively, and first ends of the first medicinal fluid delivery lines 130A, 130B, and 130C may be connected to the diverging pipes 263, respectively.

For example, the flow speed at a medicinal fluid in any one of the flow rate control pipes 262 of the medicinal fluid distributor 260 may be set at 1 mL/h and the flow speed of a medicinal fluid in the other one may be set at 2 mL/h.

The first medicinal fluid converger 265 may be composed of a converging pipe 265, a diverging pipe 267 diverging from the converging pipe 266, and three flow rate control pipe 268. The second medicinal fluid converger 365 may be composed of a converging pipe 366 and two diverging pipes 367 diverging from the converging pipe 366.

In the first medicinal fluid converger 265, a medicinal fluid inflow hose 4 may be connected to the converging pipe 266 and second ends of the first medicinal fluid delivery lines 130A, 130B, and 130C may be connected to the flow rate control pipes 268, respectively. Further, second ends of the second medicinal fluid delivery lines 330A and 330B may be connected to the diverging pipes 367 of the second medicinal fluid converger 365, respectively.

Both ends of a converging line 81-1 may be connected to the diverging pipe 267 of the first medicinal fluid converger 265 and the converging pipe 366 of the second medicinal fluid converger 365, respectively.

The medicinal fluid pumping unit 82 of the bolus apparatus is disposed in the converging line 81-1.

According to this medicinal fluid injector, the second medicinal fluid flow rate control apparatus is set in the off-mode (0 mL/h) when the bolus apparatus is not used, whereby it is possible to a medicinal fluid from flowing into and being kept in the bolus bag 83 of the medicinal fluid pumping unit 82.

When using the medicinal fluid injector for pain management, a user frequently presses the push button 84 to attenuate a pain when he/she feels severe pain. Then, a medicinal fluid may be excessively given to the patient. In this case, when the medicinal fluid injector is set such that a medicinal fluid is supplied into the bolus bag at a relatively small flow rate (for example, 1 mL/h) by the second medicinal fluid flow rate control apparatus, it takes relatively long time to fill the bolus bag 83 with the medicinal fluid, so even if the patient presses the push button 84, the medicinal fluid is not additively injected in response to the operation, and accordingly, excessive injection of the medicinal fluid into him/herself can be prevented.

Although the present invention was described above, the present invention is not limited to the embodiments described above and the accompanying drawings and may be modified in various ways by those skilled in the art without departing from the spirit of the present invention.

What is claimed is:

1. A medicinal fluid flow rate control apparatus, comprising:
    a case having an upper wall portion, a lower wall portion, and a side wall portion extending between the upper and lower wall portions and defining a circumferential boundary of the case;
    an operation knob having a cylindrical outer surface, the operation knob disposed rotatably about a vertical rotation axis in the case and exposed through an opening at the upper wall portion;
    a tube support member placed at one lateral side of the side wall portion of the case, the tube support member including a plurality of tube seating grooves vertically spaced apart to one another, each tube seating groove linearly extending in a direction perpendicular to the vertical rotation axis of the operation knob;
    a plurality of medicinal fluid delivery lines each having an elastically deformable tube, the elastically deformable tubes affixed in corresponding tube seating grooves of the tube support member at different heights at said one lateral side of the side wall portion of the case, and allowing medicinal fluid to flow at different flow rates through the medicinal fluid delivery lines;
    a medicinal fluid converger adapted to converge the medicinal fluids from the medicinal fluid delivery lines to discharge the medical fluids through one discharge line;
    a plurality of spring plates vertically spaced apart to one another in vertical alignment and positioned at the heights corresponding to the elastically deformable tubes, respectively, between the elastically deformable tubes and the cylindrical outer surface of the operation knob, the spring plates each having a convex projection at one side, and a pressing portion at another side which is adapted to press its corresponding elastically deformable tube to block the corresponding medicinal fluid delivery lines as the spring plate is elastically bent toward the tubes when the spring plate is in contact with the cylindrical outer surface of the operation knob; and
    a preset number of recessions formed in a concave shape on the cylindrical outer surface of the operation knob at predetermined positions and at the heights corresponding to the spring plates, allowing the corresponding plate springs to elastically retract so that the tubes pressed by the spring plates are released, when the operation knob is turned and the recessions align with the corresponding convex projections of the spring plates, and selectively enabling to retract all of the spring plates from pressing or keeping selected ones of the spring plates in pressing position, depending on a rotational angle of the operation knob, thereby enabling selective opening and closing of the medicinal fluid delivery lines to control a flow rate of the medicinal fluid discharging through the medicinal fluid converger.

2. The apparatus of claim 1, wherein the pressing portion of each spring plate is provided at a central area of the spring plate, and the convex projection of each spring plate is provided at an opposite side of the pressing portion.

3. The apparatus of claim 1, wherein coupling steps are disposed at both sides of the tube support member on an inner side of the case to form grooves between the inner side of the case and the coupling steps, and wherein an extended tab is provided at both side ends of the tube support member to fit in grooves formed by the coupling steps by sliding.

4. The apparatus of claim 1, further comprising an operation handle for turning the operation knob,
wherein a top portion of the operation knob is positioned inside the opening at the upper wall portion of the case,
wherein a coupling groove is vertically formed on the top portion of the operation knob, and
wherein the operation handle has a coupling rod having a shape corresponding to the coupling groove and being fitted into the coupling groove to turn the operation knob.

5. The apparatus of claim 1, further comprising a rotational angle determiner for determining a rotational position of the operation knob at predetermined angles between the case and the operation knob.

6. The apparatus of claim 5, wherein the rotational angle determiner includes:
a plurality of locking grooves formed at predetermined angles along a bottom edge of the operation knob; and
a locking projection formed on the case to be fitted into at least any one of the locking grooves, depending on the rotational angle of the operation knob.

7. A medicinal fluid injector, comprising:
at least one first delivery line diverging from a medicinal fluid inflow line and connected to a medicinal fluid discharge line;
a case having an upper wall portion, a lower wall portion, and a side wall portion extending between the upper and lower wall portions and defining a circumferential boundary of the case;
an operation knob having a cylindrical outer surface, the operation knob disposed rotatably about a vertical rotation axis in the case and exposed through an opening at the upper wall portion;
a tube support member placed at one lateral side of the side wall portion of the case, the tube support member including a plurality of tube seating grooves vertically spaced apart to one another, each tube seating groove linearly extending in a direction perpendicular to the vertical rotation axis of the operation knob;
a plurality of second delivery lines diverging from the medicinal fluid inflow line, each having an elastically deformable tube, the elastically deformable tubes affixed in corresponding tube seating grooves of the tube support member at different heights at said one lateral side of the side wall portion of the case, and allowing medicinal fluid to flow at different flow rates through the second delivery lines;
a medicinal fluid converger adapted to converge medicinal fluids from the second delivery lines, and a medicinal fluid converging line supplying the medicinal fluid from the medicinal fluid converger to the medicinal fluid discharge line;
a medicinal fluid pumping unit disposed in the medicinal fluid converging line and having a bolus bag keeping the medicinal fluid from the second delivery lines and pumping the kept medicinal fluid to the medicinal discharge line when an external force is applied;

a plurality of spring plates vertically spaced apart to one another in vertical alignment and positioned at the heights corresponding to the elastically deformable tubes, respectively, between the elastically deformable tubes and the cylindrical outer surface of the operation knob, the spring plates each having a convex projection at one side, and a pressing portion at another side which is adapted to press its corresponding elastically deformable tube to block the corresponding second delivery lines as the spring plate is elastically bent toward the tubes when the spring plate is in contact with the cylindrical outer surface of the operation knob; and
a preset number of recessions formed in a concave shape on the cylindrical outer surface of the operation knob at predetermined positions and at the heights corresponding to the spring plates, allowing the corresponding plate springs to elastically retract so that the tubes pressed by the spring plates are released, when the operation knob is turned and the recessions align with the corresponding convex projections of the spring plates, and selectively enabling to retract all of the spring plates from pressing or keeping selected ones of the spring plates in pressing position, depending on a rotational angle of the operation knob, thereby enabling selective opening and closing of the second delivery lines to control a flow rate of the medicinal fluid from the medicinal fluid converger to the bolus bag.

8. The injector of claim 7, wherein the pressing portion of each spring plate is provided at a central area of the spring plate, and the convex projection of each spring plate is provided at an opposite side of the pressing portion.

9. The injector of claim 7, wherein coupling steps are disposed at both sides of the tube support member on an inner side of the case to form grooves between the inner side of the case and the coupling steps, and
wherein an extended tab is provided at both side ends of the tube support member to fit in grooves formed by the coupling steps by sliding.

10. The injector of claim 7, further comprising an operation handle for turning the operation knob,
wherein a top portion of the operation knob is positioned inside the opening at the upper wall portion of the case,
wherein a coupling groove is vertically formed on the top portion of the operation knob, and
wherein the operation handle has a coupling rod having a shape corresponding to the coupling groove and being fitted into the coupling groove to turn the operation knob.

11. The injector of claim 7, further comprising at least one seat cover coupled to the tube support member to prevent the elastically deformable tubes from separating from the tube seating grooves, and wherein both lateral ends of the spring plates are connected to the seat cover.

12. The apparatus of claim 1, further comprising at least one seat cover coupled to the tube support member to prevent the elastically deformable tubes from separating from the tube seating grooves, and wherein both lateral ends of the spring plates are connected to the seat cover.

* * * * *